(12) United States Patent
Hadfield et al.

(10) Patent No.: US 6,337,194 B1
(45) Date of Patent: Jan. 8, 2002

(54) METHOD FOR THE PREPARATION OF INSULIN BY CLEAVAGE OF A FUSION PROTEIN AND FUSION PROTEINS CONTAINING INSULIN A AND B CHAINS

(75) Inventors: Christopher Hadfield; Peter A Meacock, both of Leicester (GB); Patnam R Krishnaswamy; Kaithamana Shashi, both of Bangalore (IN); Krisha K Raina, Maharastra (IN); Candadai S Ramadoss, Bangalore (IN)

(73) Assignees: Vittal Mallya Scientific Research Foundation (IN); the University of Leicester (GB)

( * ) Notice: Subject to any disclaimer, the term of this patent is extended or adjusted under 35 U.S.C. 154(b) by 0 days.

(21) Appl. No.: 08/981,988

(22) PCT Filed: Jul. 8, 1996

(86) PCT No.: PCT/GB96/01620

§ 371 Date: Aug. 19, 1998

§ 102(e) Date: Aug. 19, 1998

(87) PCT Pub. No.: WO97/03089

PCT Pub. Date: Jan. 30, 1997

(30) Foreign Application Priority Data

Jul. 8, 1995 (GB) ............................................ 9513967

(51) Int. Cl.[7] .......................... C12N 15/17; C12N 21/04
(52) U.S. Cl. ................ 435/69.7; 435/69.4; 435/320.1; 435/254.2; 530/399; 530/350; 536/23.5
(58) Field of Search ................................. 530/350, 399; 536/23.5; 435/320.1, 69.7, 69.4, 254.2

(56) References Cited

U.S. PATENT DOCUMENTS 5,563,123 A * 10/1996 Innis et al. ................... 514/12

FOREIGN PATENT DOCUMENTS

| EP | 0 195 691 | * | 9/1986 |
| EP | A-0518587 | * | 12/1992 |
| WO | WO 84/03103 | * | 8/1984 |

OTHER PUBLICATIONS

Leninger, Biochemistry, Second Edition, see p. 109, Fig. 5–13, 1975.*

* cited by examiner

Primary Examiner—Lorraine Spector
Assistant Examiner—Eileen B. O'Hara
(74) Attorney, Agent, or Firm—Jones, Day, Reavis & Pogue

(57) ABSTRACT

The invention provides a protein precursor of a double-chain molecule having at least two polypeptide chains linked by two disulfide bonds. The precursor has the general formula B—Z—A wherein B and A are the two insulin polypeptide chains, and Z is a polypeptide comprising at least one site for proteolytic cleavage in a eukaryotic host cell transformed by DNA coding for the protein precursor or in a eukaryotic cell-free system, resulting in a secreted double-chain product consisting of the disulfide-bonded A and B chains in which a portion of the Z polypeptide is retained on the A chain and/or the B chain and can be removed therefrom by enzymatic or chemical agents in vitro. Preferably the B and A polypeptides are, respectively, the B- and A-chains of insulin linked by two disulfide bonds, and the mature insulin molecule is isolatable from the secreted double-chain product. Preferably, the retained portion of the Z polypeptide comprises an affinity polypeptide tag for isolation and purification of the double-chain product. The Z polypeptide may further comprise an additional isolatable polypeptide of interest. The invention provides DNA sequences encoding the protein precursor, organisms transformed and transfected therewith and methods for preparing insulin from the protein precursor.

53 Claims, 19 Drawing Sheets

FIG. 2

Ins1 sequence

B-chain
Phe Val Asn Gln His Leu Cys Gly Ser His Leu Val Glu Ala Leu Tyr Leu Val Cys Gly Glu Arg Gly Phe
TTC GTT AAC CAA CAC TTG TGT GGT TCT CAC TTG GTT GAA GCC TTG TAC TTG GTT TGT GGT GAA AGA GGT TTC 'mini C'
Phe Tyr Thr Pro Lys Thr    Lys Arg
TTC TAC ACT CCA AAG ACT    AAG AGA A-chain
Gly Ile Val Glu Gln Cys Cys Thr Ser Ile Cys Ser Leu Tyr Gln
GGT ATC GTT GAA CAA TGT TGT ACT TCT ATC TGT TCT TTG TAC CAA Leu Glu Asn Tyr Cys Asn  ***
TTG GAA AAC TAC TGT AAC  TAA

FIG. 5

Ins2 sequence

B-chain
Phe Val Asn Gln His Leu Cys Gly Ser His Leu Val Glu Ala Leu Tyr Leu Val Cys Gly Glu Arg Gly Phe
TTC GTT AAC CAA CAC TTG TGT GGT TCT CAC TTG GTT GAA GCC TTG TAC TTG GTT TGT GGT GAA AGA GGT TTC 9E10 epitope
Phe Tyr Thr Pro Lys Thr   Met His Glu Gln Lys Leu Ile Ser Glu Glu Asp Leu Val Asp Lys Arg
TTC TAC ACT CCA AAG ACT   ATG CAT GAA CAA AAG TTG ATC TCT GAA GAA GAC TTG GTC GAC AAG AGA
                          NsiI                                                  SalI A-chain
Gly Ile Val Glu Gln Cys Cys Thr Ser Ile Cys Ser Leu Tyr Gln
GGT ATC GTT GAA CAA TGT TGT ACT TCT ATC TGT TCT TTG TAC CAA Leu Glu Asn Tyr Cys Asn   ***
TTG GAA AAC TAC TGT AAC   TAA

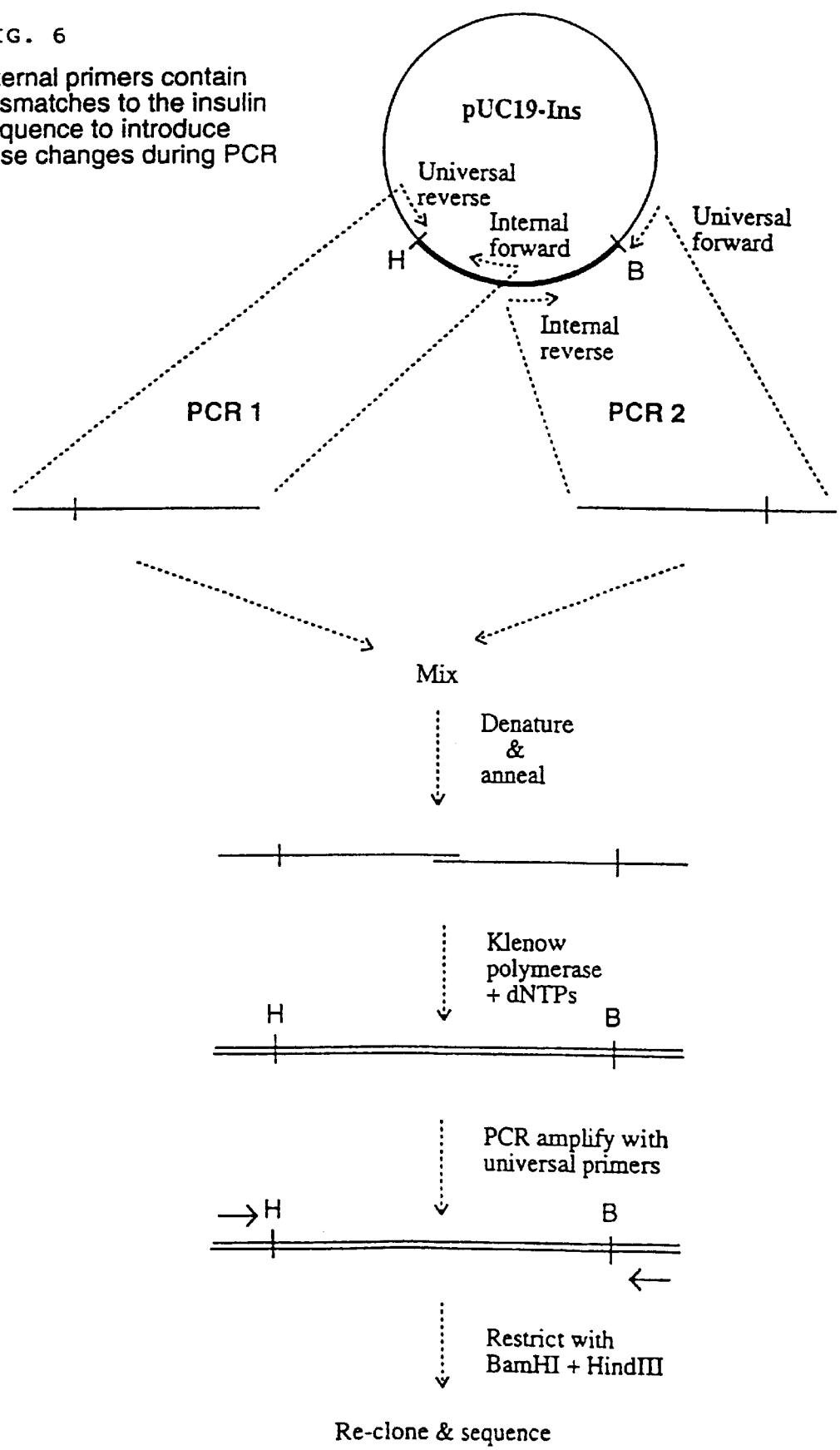

FIG. 7

Derivation of Ins3

Ins3 was made by PCR mutagenesis of Ins2, using the general strategy.

B-MetHis-9E10-LysArg-A  →  B-LysArg-9E10-LysArg-A

The internal primers for the mutagenesis were:

```
              Lys  Arg
               ⇑    ⇑                              →
         5'ACTAAG AGAGAACAAAAGTTGATCTCTG3'
      3'GAAGATGTGAGGTTTCTGATTC TCTCTT5'
      ←
                 12 bp overlap
```

Derivation of Ins4

Ins4 was made by PCR mutagenesis of Ins3, using the general strategy.

B-LysArg-9E10-LysArg-A  →  B-LysArg-9E10-Met-A

The internal primers for the mutagenesis were:

```
                 Met
                  ⇑                    →
         5'GACAAG ATG GGTATCGTTGAACAA3'
      3'CTTCTGAACCAGCTGTTC TAC CCA5'
      ←
              12 bp overlap
```

FIG. 8

Ins3 sequence

B-chain
Phe Val Asn Gln His Leu Cys Gly Ser His Leu Val Glu Ala Leu Tyr Leu Val Cys Gly Glu Arg Gly Phe
TTC GTT AAC CAA CAC TTG TGT GGT TCT CAC TTG GTT GAA GCC TTG TAC TTG GTT TGT GGT GAA AGA GGT TTC 9E10 epitope
Phe Tyr Thr Pro Lys Thr    Lys Arg Glu Gln Lys Leu Ile Ser Glu Glu Asp Leu Val Asp Lys Arg
TTC TAC ACT CCA AAG ACT    AAG AGA GAA CAA AAG TTG ATC TCT GAA GAA GAC TTG GTC GAC AAG AGA
                                                                          Sal I A-chain
Gly Ile Val Glu Gln Cys Cys Thr Ser Ile Cys Ser Leu Tyr Gln Leu Glu Asn Tyr Cys Asn  ***
GGT ATC GTT GAA CAA TGT TGT ACT TCT ATC TGT TCT TTG TAC CAA TTG GAA AAC TAC TGT AAC  TAA

FIG. 9

Ins4 sequence

B-chain
Phe Val Asn Gln His Leu Cys Gly Ser His Leu Val Glu Ala Leu Tyr Leu Val Cys Gly Gly Glu Arg Gly Phe
TTC GTT AAC CAA CAC TTG TGT GGT TCT CAC TTG GTT GAA GCC TTG TAC TTG GTT TGT GGT GAA AGA GGT TTC 9E10 epitope
Phe Tyr Thr Pro Lys Thr   Lys Arg Glu Gln Lys Leu Ile Ser Glu Glu Asp Leu Val Asp Lys Met
TTC TAC ACT CCA AAG ACT   AAG AGA GAA CAA AAG TTG ATC TCT GAA GAC TTG GTC GAC AAG ATG
                                                                        SalI A-chain
Gly Ile Val Glu Gln Cys Cys Thr Ser Ile Cys Ser Leu Tyr Gln Leu Glu Asn Tyr Cys Asn  ***
GGT ATC GTT GAA CAA TGT TGT ACT TCT ATC TGT TCT TTG TAC CAA TTG GAA AAC TAC TGT AAC  TAA Ins5

B--MetHis-9E10-Pur-LysArg--A

Derived from Ins2 via insertion of double-stranded synthetic oligonucleotide (Pur) into SalI site.

Pur sequence:

```
    (Val) Asp Met His Gly Leu Arg Ala Arg Asn Arg Ser Lys Thr Gly Pro (Val Asp)
     TC  GAC ATG CAT GGT TTG AGA GCT AGA AAC AGA TCT AAG ACC GGT CCA G
     G   CTG TAC GTA CCA AAC TCT CGA TCT TTG TCT AGA TTC TGG CCA GGT CAG CT
     SalI     NsiI                              BglII                    SalI
```

FIG. 11

Ins5 sequence

*B-chain*

Phe Val Asn Gln His Leu Cys Gly Ser His Leu Val Glu Ala Leu Tyr Leu Val Cys Gly Glu Arg Gly Phe
TTC GTT AAC CAA CAC TTG TGT GGT TCT CAC TTG GTT GAA GCC TTG TAC TTG GTT TGT GGT GAA AGA GGT TTC

*9E10 epitope*

Phe Tyr Thr Pro Lys Thr    Met His Glu Gln Lys Leu Ile Ser Glu Glu Asp Leu
TTC TAC ACT CCA AAG ACT    <u>ATG CAT</u> GAA CAA AAG TTG ATC TCT GAA GAA GAC TTG
                           *Nsil*

*Purification tag*

Gly Leu Arg Ala Arg Asn Arg Ser Lys Thr Gly Pro    Val Asp Lys Arg
         GGT TTG AGA GCT AGA AAC AGA <u>TCT</u> AAG ACC GGT CCA    <u>GTC GAC</u> AAG AGA
                                 *BglII*                          *SalI*

Val Asp Met His    Gly
<u>GTC GAC</u> <u>ATG CAT</u>    GGT
*SalI*    *Nsil*

*A-chain*

Gly Ile Val Glu Gln Cys Cys Thr Ser Ile Cys Ser Leu Tyr Gln Leu Glu Asn Tyr Cys Asn ···
GGT ATC GTT GAA CAA TGT TGT ACT TCT ATC TGT TCT TTG TAC CAA TTG GAA AAC TAC TGT AAC TAA

FIG. 13

Ins6 sequence

B-chain
Phe Val Asn Gln His Leu Cys Gly Ser His Leu Val Glu Ala Leu Tyr Leu Val Cys Gly Glu Arg Gly Phe
TTC GTT AAC CAA CAC TTG TGT GGT TCT CAC TTG GTT GAA GCC TTG TAC TTG GTT TGT GGT GAA AGA GGT TTC 9E10 epitope
Phe Tyr Thr Pro Lys Thr    Lys Arg Glu Gln Lys Leu Ile Ser Glu Glu Asp Leu
TTC TAC ACT CCA AAG ACT    AAG AGA GAA CAA AAG TTG ATC TCT GAA GAA GAC TTG Purification tag
Val Asp Met His    Gly Leu Arg Ala Arg Asn Arg Ser Lys Thr Gly Pro    Val Asp Lys Met
GTC GAC ATG CAT    GGT TTG AGA GCT AGA AAC AGA TCT AAG ACC GGT CCA    GTC GAC AAG ATG
SalI   Nsil                                 BgIII                     SalI A-chain
Gly Ile Val Glu Gln Cys Cys Thr Ser Ile Cys Ser Leu Tyr Gln Leu Glu Asn Tyr Cys Asn ***
GGT ATC GTT GAA CAA TGT TGT ACT TCT ATC TGT TCT TTG TAC CAA TTG GAA AAC TAC TGT AAC TAA

FIG. 15 ins7 sequence

B-chain
Phe Val Asn Gln His Leu Cys Gly Ser His Leu Val Glu Ala Leu Tyr Leu Val Cys Gly Glu Arg Gly Phe
TTC GTT AAC CAA CAC TTG TGT GGT TCT CAC TTG GTT GAA GCC TTG TAC TTG GTT TGT GGT GAA AGA GGT TTC Purification tag
Phe Tyr Thr Pro Lys Thr    Lys Arg    Gly Leu Arg Ala Arg Asn Arg Ser Lys Thr Gly Pro    Val Asp Lys Met
TTC TAC ACT CCA AAG ACT    AAG AGA    GGT TTG AGA GCT AGA AAC AGA TCT AAG ACC GGT CCA GTC GAC AAG ATG

*BglII* (AGA TCT) *SalI* (GTC GAC)

*A-chain*

Gly Ile Val Glu Gln Cys Cys Thr Ser Ile Cys Ser Leu Tyr Gln Leu Glu Asn Tyr Cys Asn ***
GGT ATC GTT GAA CAA TGT TGT ACT TCT ATC TGT TCT TTG TAC CAA TTG GAA AAC TAC TGT AAC TAA

FIG. 16

Ins8

Porcine insulin precursor derived from Ins4

B_pig - LysArg - 9E10 - Met - A

PCR mutagenesis of Ins4 : B30Thr→Ala

Ins9

Porcine insulin precursor derived from Ins6

B_pig - LysArg - 9E10 - Pur - Met - A

PCR mutagenesis of Ins6 : B30Thr→Ala

Primers for Ins8 and Ins9 derivation:

```
                  Ala
       5'AAG GCC AAGAGAGAACAAAAGTTGATC3'
   3'TCCAAAGAAGATGTGAGGTTTC CGG TTC5'
```

FIG. 17                    Ins10

Bovine insulin precursor derived from Ins9

Bpig/bovine - LysArg - 9E10 - Pur - Met - Abovine

PCR mutagenesis of Ins9 : A8Thr→Ala A10Ile→Val

Primers:

```
                  Ala        Val
        5'GTTGT GCT TCT GTT TGTTCTTTGTACCAA3'
3'GCAACTTGTTACAACA CGA AGA CAA ACAAG5'
```

FIG. 19

MFα secretion leader / synthetic insulin coding sequence fusions pDP314 constructs

```
              KEX2       STE13     STE13
               ⇓           ↓         ↓
        Lys   Arg   Glu   Ala   Glu   Ala   Phe
       ...AAG  AGA  GAG  GCT  GA A  GCT  TTC...
       ...TTC  TCT  CTC  CGA  CT T  CGA  AAG...
            MFα prepro leader            Ins sequence
``` pDP315 constructs

```
              KEX2
               ⇓
        Lys   Arg   Phe
       ...AAG  AGA  TTC...
       ...TTC  TCT  AAG...
        MFα prepro leader   Ins sequence
``` pDP316 constructs

```
              signal
             peptidase
                ⇓
        Ala   Ala   Phe
       ...GCT  GCG  TTC...
       ...CGA  CGC  AAG...
        MFα pre leader   Ins sequence
```

METHOD FOR THE PREPARATION OF INSULIN BY CLEAVAGE OF A FUSION PROTEIN AND FUSION PROTEINS CONTAINING INSULIN A AND B CHAINS

The present invention concerns double-chain disulfide-bonded molecules, particularly insulin, and precursor molecules for same, together with DNA sequences coding for same, processes for preparation of said precursors, and processes for the preparation of the molecule.

Human insulin is a non-steroidal hormone comprising two polypeptide chains (A and B); the A-chain comprising 21 amino acid residues ($A_{1-2}$) and the B-chain comprising 30 amino acid residues ($B_{1-30}$) The A- and B-chains are joined by two intermolecular disulfide bridges. A third intramolecular disulfide bridge is formed within the A-chain.

Human insulin is naturally produced in the pancreas by the β-cells of the islets of Langerhans, via. a single 110 amino acid precursor polypeptide (preproinsulin) (Chan, S. J. et al., 1976, Proc. Natl. Acad. Sci. USA, 73: 1964–1968; Sheilds and Blobel, 1977, Proc. Natl. Acad. Sci. USA, 74: 2059–2063) with a structure of:

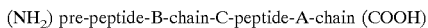

($NH_2$) pre-peptide-B-chain-C-peptide-A-chain (COOH)

The human preproinsulin (precursor) undergoes various post-translational modifications and events to convert it into mature insulin. The first step is removal of the prepeptide (Bell, G. I. et al., 1979, Nature 282: 525–527), which acts as a signal sequence to direct the molecule (proinsulin) upon synthesis into the endoplasmic reticulum (ER) and hence into the secretory pathway. After entry into the ER, the resultant proinsulin then folds and the three disulfide bridges are formed (Chan et al., 1976, supra; Lomedico, P. T. et al., 1977, J. Biol. Chem., 259: 7971–7978; Shields and Bloebel, 1977 supra). The proinsulin then passes to the Golgi, is packaged into secretory granules and is converted into mature insulin by endoproteolytic cleavage (Steiner, D. F. et al., 1984, J. Cell. Biol., 24: 121–130; Tager and Steiner, 1974, Ann. Rev. Biochem., 43: 509–538).

Since the discovery of insulin in 1921, the nature of insulin preparations used to treat diabetics has shown a steady evolution (Owens, D. R., 1986, Human Insulin, pp 5–33 MTP Press). A human source of insulin has always been impractical due to low yields from the pancreas and degradation. However, the structure of insulin is highly conserved in other mammals, making it possible to use other animals as a source of insulin. This has led to the development of porcine and bovine insulins. However, they are difficult to manufacture, great care having to be taken to ensure purity and to minimise their allergic response.

Latterly, recombinant DNA methods have allowed the synthesis of various forms of recombinant human insulin. This has been achieved using *E. coli* and *Saccharomyces cerevisiae*. Early techniques involved the production of separate A- and B-chains (Goeddel, D., et al., 1979, Proc. Natl. Acad. Sci. USA, 76: 106–110; Chance, R. E. et al., 1981, In: Rich, D. H. & Gross, E. (eds.) Peptides: Synthesis-Structure-Function, Proc. Seventh American Peptide Symposium, pp 721–728, Rockford II, Pierce Chemical Co.; Frank, B. H. et al., 1981, In. Rich, D. H. & Gross, E. (eds.) Peptides: Synthesis-Structure-Function, Proc. Seventh American Peptide Symposium, pp 729–738. Rockford II, Pierce Chemical Co.; Steiner, D. F., et al., 1968, Proc. Natl. Acad. Sci. USA, 60: 622; and EP-A-0 090 433).

However, these procedures, all of which require the chemical combination of the A- and B-chains, have several serious drawbacks. One is that the fusion proteins accumulate intracellularly and are subject to proteolytic degradation. They must all be purified from the other intracellular materials, and *E. coli* materials are pyrogenic. Additionally, chemical dusulfide bond formation is inefficient.

An alternative approach has been to produce insulin from eukaryotic cells and utilise the secretion pathway to modify precursor insulin into the mature form as happens in the pancreatic β-cells and also to secrete the product into the culture medium, away from the intracellular proteins, where there are few contaminants from which it needs to be purified. Examples of such work include EP 0 121 884 A; EP 0 195 691 A; Wollmer, A., et al., 1974, Hoppe-Seyler's Z. Physiol. Chem., 355: 1471–1476; Brandenburg, D. et al., 1973, Hoppe-Seyler's Z. Physiol. Chem., 354:1521–1524; Thim, L., et al., 1986, Proc. Natl. Acad. Sci. USA, 83: 6766–6770; Thim, L., et al., 1987, FEBS, Let 212: 307–312; EP 0 163 529 A; EP 0 427 296 A; Markussen, J., et al., 1986, (In Peptides, 1986, Theodoropoulos, D., (ed.) pp. 189–194, Proc. 19th Eur. Peptide Symp. on Peptide, Porto Carras-Chalkidiki, Greece. Walter de Gruyter & Co, New York) and EP 0 347 845 A. FIGS. 1 and 2 show a mini-proinsulin (Thim, L. et al., 1986, supra).

However, these are unable to give high yields of mature insulin or near-mature insulin, instead being primarily concerned with producing high levels of insulin precursors (for example, insulin precursors with the carboxy-terminus residue of the B-chain ($B_{30}$) missing) which subsequently require costly and extensive chemical alteration in order to convert them into mature insulin. The present invention overcomes the limitations and disadvantages of the prior art and provides simple, convenient and economic double-chain molecules and precursor molecules, in particular insulin, together with DNA sequences coding for same, processes for preparation of said precursors, and processes for the preparation of insulin and insulin analogues.

According to the present invention there is provided a protein precursor for at least two polypeptide chains having the general formula B-Z-A wherein B and A are the two polypeptide chains of a double-chain molecule, the two chains being linked by at least one disulfide bond, and Z is a polypeptide comprising at least one proteolytic cleavage site.

The precursor may be produced in a host. By 'host' is meant a system which is capable of producing the protein precursor of the present invention. The host may be cells of a single- or multi-cellular organism, or it may be a cell-free system. For example, the host may be eukaryotic. It may be yeast or fungal cells or it may be an animal, for example sheep, rat or mouse, or it may be a cell-line from an animal.

Alternatively, the precursor may be produced in a cell-free host system.

Proteolytic cleavage of Z may produce the double-chain molecule, possibly in its mature form, or a near precursos thereof.

The double-chain molecule may be insulin, the B and A polypeptides representing, respectively, the B- and A-chains of insulin.

Insulin may for example be human, bovine or porcine insulin or a partially modified form thereof For example, modification may be by way of addition, deletion or substitution of amino acid residues. Substitutions may be conserved substitutions. Modification of human insulin to produce porcine insulin may be achieved by substitution of alanine at residue $B_{30}$. Bovine insulin may be produced from human insulin by substitution of alanine at residue $B_{30}$, of alanine at $A_8$ and of valine at $A_{10}$. Partially modified forms of molecules (comprising amino acid residues or nucleic acids) may be considered to be homologues of the molecules from which they were derived. The may have at least 50% homology with the molecules from which they were derived. They may for example have at least 60, 70, 80, 90 or 95% homology.

The present inventors have found that, surprisingly, despite the problems associated with the prior art synthesis of recombinant insulin, mature insulin and near-precursors of insulin may be produced in vivo in organisms such as yeast using genetic constructs, the mature insulin resulting from post-translational processing of the precursor molecule. Moreover, these insulin molecules may be produced at high yield by yeast, making the present invention an economically viable alternative to the present methods of synthesising insulin.

The polypeptide Z may also comprise at least one additional polypeptide. Hence not only may a double-chain molecule such as insulin be produced, but an additional molecule or molecules, which may also require post-translational processing, may be produced.

The polypeptide Z may also comprise a purification sequence. The purification sequence may, for example, bind to heparin and/or phosvitin. The purification sequence may be a sequence which is recognised and bound by another molecule. This allows the purification sequence, and therefore the rest of the protein precursor, to be readily purified from a mixture which may contain various contaminants. The mixture may, for example, be a cell lysate.

The polypeptide Z may be of the general formula (I): KR-X-KR or an analogue thereof wherein K is lysine, R is arginine and X represents a chain of amino acid residues sufficient in length to facilitate cleavage in a host at the KR residues and eliminate processing losses. Analogues may of course include polypeptide Z having residues other than K and R which facilitate cleavage at the residues. Such cleavage sites, sequences and endopeptidases for achieving cleavage are well known.

Such a protein precursor may for example have the formula of Ins3 (FIG. 8; SEQ ID NO: 1) or a partially modified form thereof.

The polypeptide Z may be of the general formula (II): KR-X-M or an analogue thereof wherein K is lysine, R is arginine, M is methionine and X represents a chain of amino acid residues sufficient in length to facilitate cleavage in a host at the KR residue.

Such a protein precursor may for example have the formula of Ins4 (FIG. 9; SEQ ID NO: 2), Ins6 (FIG. 13; SEQ ID NO: 3) and Ins7 (FIG. 15; SEQ ID NO: 4) or a partially modified form thereof.

Alternatively, such a protein precursos could be for porcine insulin and have the sequence of Ins8 (FIG. 16; SEQ ID NO: 7) or Ins9 (FIG. 16; SEQ ID NO: 8). Similarly, it could be for bovine insulin and have the sequence of Ins10 (FIG. 17; SEQ ID NO: 9).

The polypeptide Z may be of the general formula (III): KR-Pur-M or an analogue thereof wherein K is lysine, R is arginine, Pur is a purification sequence, and M is methionine.

Treatment of such a protein precursor with for example cyanogen bromide may both cleave off the Pur purification sequence and simultaneously produce the mature double-chain molecule or a near precursor thereof.

By 'near presursor thereof' is meant a precursor of the double-chain molecule which may be simply converted into its mature state by, for example, treatment with a protease or proteases. For example, the double-chain molecule may be insulin, a near precursor being converted to mature insulin by treatment with carboxypeptidase B alone or by trypsin plus carboxypeptidase B.

Such a protein precursor may have the formula of Ins7 (FIG. 15; SEQ ID NO: 4) or a partially modified form thereof.

The polypeptide Z may be of the general formula (IV): KR-Y-M or an analogue thereof (for example having substitutions at K, R or M) wherein K is lysine, R is arginine, Y is a second polypeptide, and M is methionine.

Treatment of such a protein precursor with for example cyanogen bromide may produce the mature double-chain molecule and release the second polypeptide.

In such a protein precursor, Y may be a c-myc peptide sequence, the precursor having the formula of Ins4 (FIG. 9; SEQ ID NO: 2) or a partially modified form thereof.

The polypeptide Z may be of the general formula (V): KR-Y-N-Pur-M or an analogue thereof wherein K is lysine, R is arginine, Y is a second polypeptide, N is methionine or aspartic acid, Pur is a purification sequence, and M is methionine.

N may be methionine and treatment with for example cyanogen bromide may cause cleavage of the purification sequence from the second polypeptide.

N may be aspartic acid and treatment with for example *Pseudomonas fragi* mutant Me1 endopeptidase may cause cleavage of the purification sequence from the second polypeptide.

Y may for example be a c-myc peptide sequence, the purification sequence Pur binding specifically to heparin and phosvitin, the precursor having the formula of Ins6 (FIG. 13; SEQ ID NO: 3) or a partially modified form thereof.

The polypeptide Z may be of the general formula (VI): N-X-KR or an analogue thereof wherein N is methionine or aspartic acid, K is lysine, R is arginine, and X is a chain of amino acid residues sufficient in length to facilitate cleavage in a host at the KR residues.

The chain X of amino acid residues may comprise a purification sequence and/or a second polypeptide.

Such a protein precursor may have the formula of Ins2 (FIG. 5; SEQ ID NO: 5) or of Ins5 (FIG. 11; SEQ ID NO: 6) or a partially modified form thereof.

Additionally, a protein precursor according to the present invention may also comprise a leader peptide which directs the protein precursor into the secretion pathway of a host.

In analogues of formulae (I)—(VI), amino acid residues K, R, M and N may be substituted with alternative residues which still allow the production of the desired end-product or products. For example, substitution of KR could be for a sequence which is proteolytically cleaved by an endopeptidase.

Also provided according to the present invention are DNA sequences encoding the protein precursors of the present invention.

Such a DNA sequence may be adapted to a host wherein the codons of the DNA sequence correspond to the most abundant transfer RNAs for each amino acid in the host.

Such a DNA sequence may be selected from any one of the group of Ins2 (FIG. 5; SEQ ID NO: 10), Ins3 (FIG. 8; SEQ ID NO: 11), Ins4 (FIG. 9; SEQ ID NO: 12), Ins5 (FIG. 11; SEQ ID NO: 13), Ins6 (FIG. 13; SEQ ID NO: 14),Ins7 (FIG. 15; SEQ ID NO: 15), Ins8 (FIG. 16; SEQ ID NO: 16), Ins9 (FIG. 16; SEQ ID NO: 17) and Ins 10 (FIG. 17; SEQ ID NO: 18) or a partially modified form thereof For example, modifications may be by way of substitution of nucleic acid bases, the substituted sequences encoding the same amino acid sequence. Partially modified forms of DNA sequences may therefore be considered to be analogues of the sequences from which they were derived. Modified sequences may for example be the addition of transcription control sequences.

Also provided are DNA sequences according to the present invention when transfected or transformed into a host organism.

Also provided are host organisms transfected or transformed with a DNA sequence according to the present invention.

Methods of transfection and transformation are well known in the art and transgenic organisms may be readily produced.

Also provided are methods of production of a double-chain molecule or a near precursor thereof comprising expressing a DNA sequence according to the present invention in a host. Such a double-chain molecule may, for example, be insulin.

Such a method may comprise transforming or transfecting a host organism with an expression vector expressing a DNA sequence according to the present invention.

Such a method of production may comprise transforming the host organism with an expression vector encoding a protein precursor wherein Z is of the general formula (I), cultivating the transformed host in a suitable culture medium, recovering the secreted product or products and converting any near precursor of insulin into insulin by teatment with carboxypeptidase B alone or by teatment with trypsin and carboxypeptidase.

Alternatively, such a method of production may comprise transforming the host organism with an expression vector encoding a protein precursor wherein Z is of the general formula (II), cultivating the transformed host in a suitable culture medium, recovering the secreted product and converting it to mature insulin by cleavage at the methionine residue with cyanogen bromide treatment in order to remove the chain of amino acid residues X.

Alternatively, such a method of production may comprise transforming the host organism with an expression vector encoding a protein precursor wherein Z is of the general formula (III), cultivating the transformed host in a suitable culture medium, recovering the secreted product via affinity-chromotography via the purification sequence Pur and converting it to mature insulin by cleavage at the methionine residue with cyanogen bromide treatment in order to remove the chain of amino acid residues X.

Alternatively, such a method of production may comprise transforming the host organism with an expression vector encoding a protein precursor wherein Z is of the general formula (IV), cultivating the transformed host in a suitable culture medium, recovering the secreted product and converting it to mature insulin and releasing the second polypeptide Y by cleavage at the methionine residue with cyanogen bromide treatment.

Alternatively, such a method of production may comprise transforming the host organism with an expression vector encoding a protein precursor wherein Z is of the general formula (V), cultivating the transformed host in a suitable culture medium, recovering the secreted product via affinity-chromotography via the purification sequence Pur, converting it to mature insulin by cleavage at the methionine residue with cyanogen bromide treatment in order to remove the chain of amino acid residues X and releasing the second polypeptide Y by cleavage at the residue N.

Alternatively, such a method of production may comprise transforming the host organism with an expression vector encoding a protein precursor wherein Z is of the general formula (VI), cultivating the transformed host in a suitable culture medium, recovering the secreted product, converting it to mature insulin by cleavage at the aspartic acid residue by *Pseudomonas fragi* Me1 endopeptidase treatment in order to remove the chain of amino acid residues X. The chain of amino acid residues X may comprise at least either a purification sequence or a second polypeptide.

The culture medium may for example be a malt-extract-cassamino acids culture medium.

The invention will be further apparent from the following description and figures which describe, by way of example only, various forms of protein precursor. Of the figures:

BRIEF DESCRIPTION OF THE DRAWINGS

FIG. 2 illustrates the DNA sequence encoding the Insl product. The amino acid and DNA sequences are SEQ ID NOs: 42 and 43 respectively;

FIG. 5 illustrates the DNA sequence (SEQ ID NO: 10) encoding the Ins2 product (SEQ ID NO: 5);

FIG. 6 illustrates the PCR mutagenesis scheme used to used to alter Ins-encoding sequences. Internal primers contain mismatches to the insulin sequence to introduce base changes during PCR;

FIG. 7 illustrates the primers used to derive Ins3 (primer SEQ ID NOs: 28 and 29) and Ins4 (primer SEQ ID NOs: 30 and 31) via in vitro mutagenesis. Ins3 was made by PCR mutagenesis of Ins2 using the general strategy and internal primers as shown. Ins4 was made by PCR mutagenesis of Ins3, using the general strategy and internal primers as shown;

FIG. 8 illustrates the DNA sequence (SEQ ID NO: 11) encoding the Ins3 product (SEQ ID NO: 1);

FIG. 9 illustrates the DNA sequence (SEQ ID NO: 12) encoding the Ins4 product (SEQ ID NO: 2);

FIG. 11 illustrates the DNA sequence (SEQ ID NO: 13) encoding the Ins5 product (SEQ ID NO: 6);

FIG. 13 illustrates the DNA sequence (SEQ ID NO: 14) encoding the Ins6 product (SEQ ID NO: 3).

FIG. 15 illustrates the DNA sequence (SEQ ID NO: 15) encoding the Ins7 product (SEQ ID NO: 4);

FIG. 16 illustrates the structure of porcine insulin precursor Ins8 derived from Ins4 and the residue of Ins4 which undergoes PCR mutagenesis, together with the structure of porcine insulin precursor Ins9 derived from Ins6 and the residue of Ins7 which undergoes PCR mutagenesis. Primers (SEQ ID NOs: 34 and 35) used to derive Ins8 and Ins9 via in vitro mutagenesis are also shown. Ins 8 has amino acid and DNA sequences SEQ ID NOs: 7 and 16. Ins 9 has amino acid and DNA sequences SEQ ID NOs: 8 and 17;

FIG. 17 illustrates the general structure of bovine insulin precursor Ins10 derived from Ins9 and the residues of Ins9 which undergoes PCR mutagenesis. Primers (SEQ ID NOs: 36 and 37) used to derive Ins10 (amino acid and DNA sequences SEQ ID NOs: 9 and 18) via in vitro mutagenesis are also shown;

FIG. 19 illustrates the MFα secretion leader/ synthetic insulin coding sequence fusions and proteolytic processing sites. The pDP314 amino acid and DNA sequences are SEQ ID NOs: 40 and 41.

EXPERIMENTAL

1. Design and Preparation of Synthetic Recombinant Insulin-encoding Sequences

The insulin-encoding sequences were sufficiently small to permit their construction via chemical synthesis. This had the advantage over using human proinsulin cDNA, as used by others, as the synthetic DNA could be designed to contain exclusively codons most highly favoured for expression in yeast. This had the advantages of facilitated maximum translation efficiency (Hoekema, A., et al., 1987, Mol. Cell. Biol. 7: 2914–2924; Hadfield, C., et al., 1993, Mycol. Res. 97: 897–944) and of minimizing possible amino acid mis-incorporation errors (Scorer, C. A., et al., 1991, Nucleic Acids Res. 19: 3511–3516). Accordingly, the insulin encoding sequences were synthesized from oligonucleotides containing codons that corresponded to the most abundant yeast transfer RNAs for each encoded amino acid (Sharp & Cowe, 1991, Yeast 7: 657–678):

```
Phe UUU/UUC      Leu UUG (UUA)
Ile AUU          Met AUG
Val GUU          Ser UCU (UCA)
Pro CCA          Thr ACU (ACA)
Tyr UAU/UAC      Ala GCU (GCC/GCA)
His CAU (CAC)    Gln CAA
Asn AAU (AAC)    Lys AAA/AAG
Asp GAU (GAC)    GIu GAA
Cys UGU          Trp UGG
Arg CGU          Ser AGU
Gly GGU
```

Stop: UAA UAA—used in tandem to ensure translation termination.
where/indicates either codon and () contains a second choice codon less frequently used in yeast.

Figure 1:
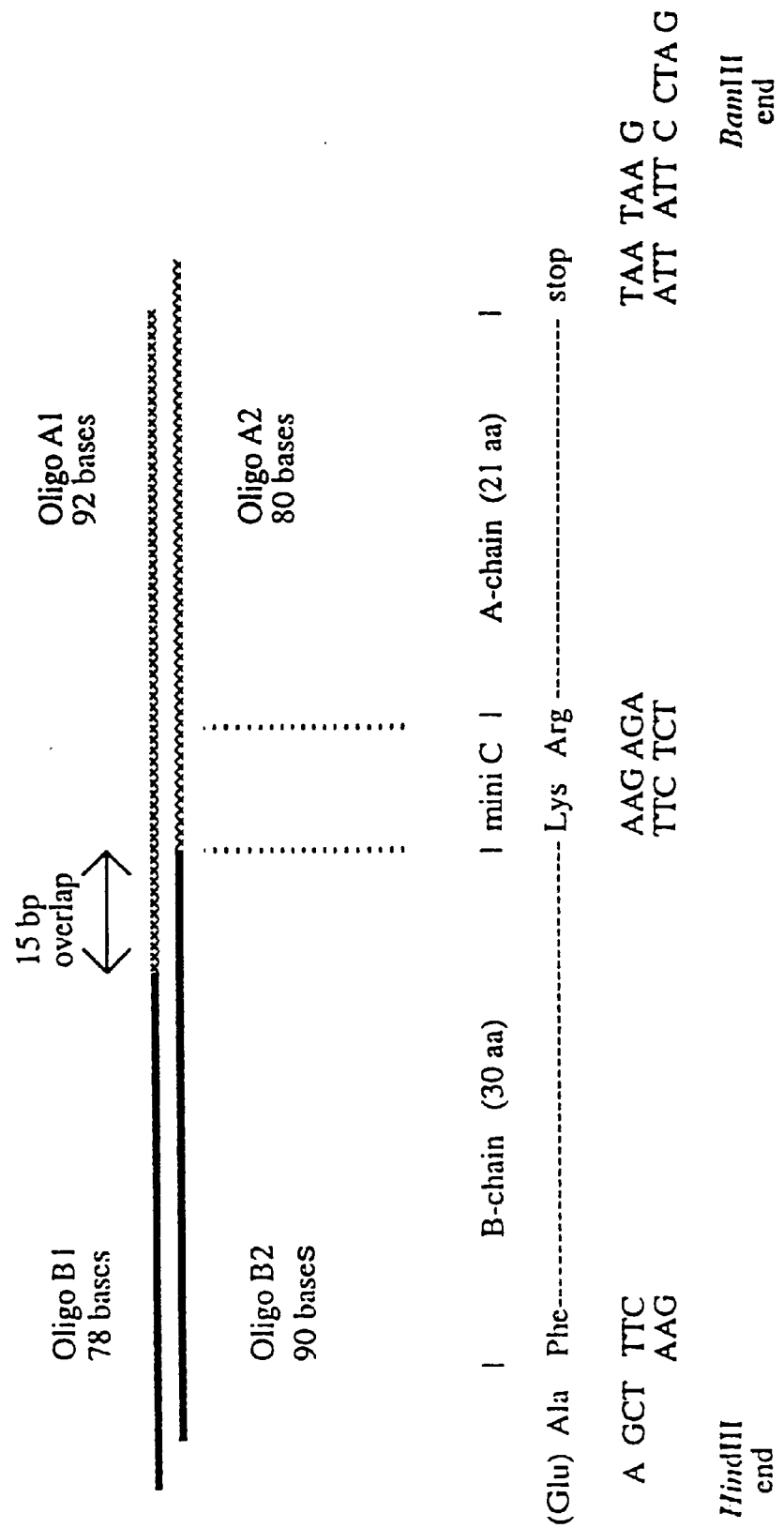
FIG. 1 illustrates the construction of Ins 1 from 4 chemically synthesized oligonucleotides.
Figure 3:
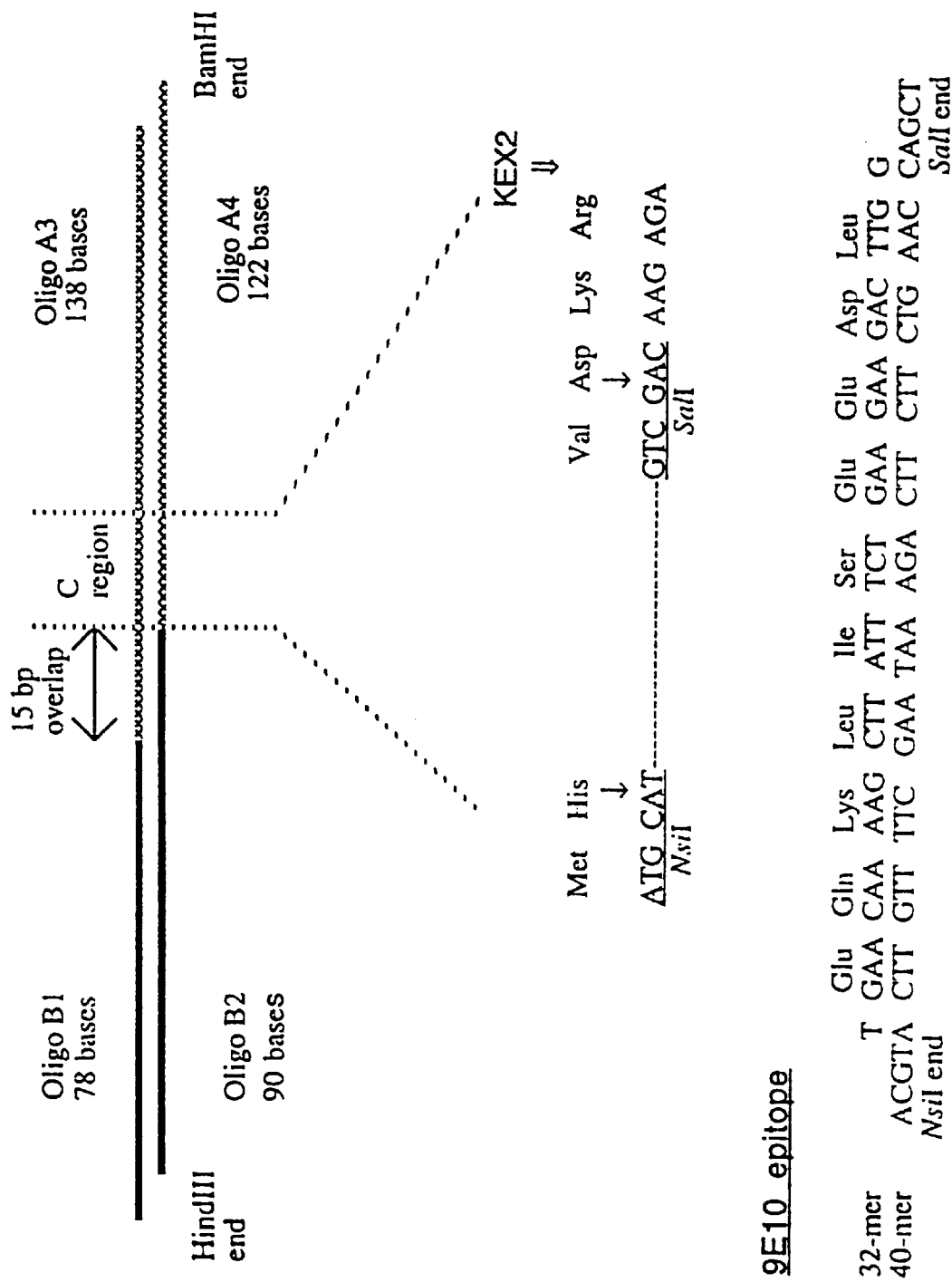
FIG. 3 illustrates the construction of Ins 2 precursors from 4 chemically synthesized oligonucleotides. The 9E10 epitope is residues 33–42 of SEQ ID NO: 5. The 32-mer is residues 96–127 of SEQ ID NO: 10. The 40-mer is the complementary sequence to residues 92–131 of SEQ ID NO: 10.

The oligonucleotides were synthesized as single strands, which were annealed together afterwards to form double-stranded DNA. Two initial insulin precursors encoding sequences were prepared in this manner, termed Ins1 and Ins2 (FIGS. 1 and 3). Each was constructed from 4 synthetic oligonucleotides (78–138 nucleotides). The synthetic DNAs were arranged to have a 5' HindIII sticky end and a 3' BamHI sticky end, enabling them to be cloned between the corresponding sites in plasmid pUC 19 and the recombinant plasmid recovered in *E. coli*.

All other insulin precursor-encoding variants were constructed by derivation from Ins2, using two methods. Firstly, Ins2 was designed to contain restriction endonuclease sites for SalI and NsiI, enabling in vitro rearrangement, or more synthetic DNA to be inserted at either of these sites via in vitro ligation. Secondly, site-directed in vitro mutagenesis methods using synthetic oligonucleotide primers were used to alter the encoding DNA (i.e. to change codons or delete DNA).

By using these methods a further eight variant insulin precursor-encoding sequences were made, termed: Ins3, Ins4, ln5, Ins6, Ins7, Ins8, Ins9, Ins 10. All of the Ins variants contained the insulin B-chain and A-chain (human for Ins1 to 7, porcine for Ins8 and 9, and bovine for Ins10), but differed in the C-peptide region, as summarized in Table 1.

C region variants contained either no sites for *S. cerevisiae* endopeptidase KEX2, one site or two sites. The KEX2 sites were Lys-Arg, the dipeptide which the endopeptidase cleaves the most efficiently (Julius, D., et al., 1984, Cell 37: 1075–1089). Ins1 encodes the mini-proinsulin of Thim, L., et al., 1986, supra, in which the B- and A chains are linked by Lys-Arg, but folding of the molecule prevents cleavage by KEX2 Other C region variants encode the 9E 10 epitope, a small c-myc peptide which is specifically recognized by a monoclonal antibody (Evan, G. I., et al., 1985, Mol. Cell. Biol. 5: 3610–3616), and/or a peptide sequence designated Pur, which binds with high specificity to phosvitin or heparin for affinity purification (see for example EP-A-91308382.0). C region variants of Ins2–10 contain between 14 and 30 amino acid residues. In Ins2 and Ins5 the KEX2 site is between the B-chain and C-peptide. In Ins4, Ins6, Ins7, Ins8, Ins9 and Ins10 the KEX2 site is between the C-peptide and the A chain. In Ins3 there are two KEX2 sites, one at each of the aforementioned positions. Ins2–16 is like Ins2 but lacks a KEX2 site.

2. Preparation of Gene and Plasmid Vector Constructs for Yeast

Figure 18:
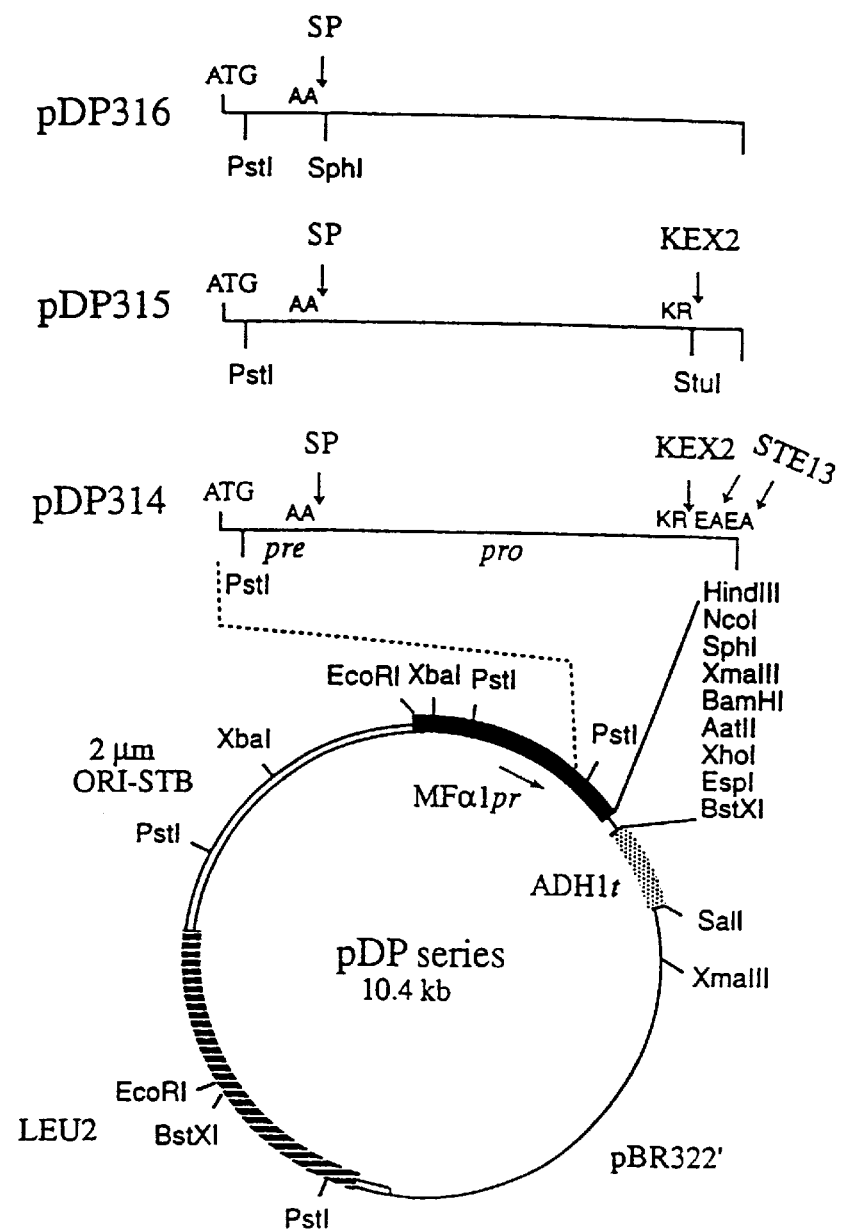
FIG. 18 illustrates the yeast expression-secretion vectors used. The HindIII cleavage site is amino acid and DNA sequences SEQ ID NOs: 38 and 39.

The synthetic insulin precursor encoding sequences were combined into yeast genes in such a way as to provide fusion to a secretion leader peptide, a promoter for transcription and a terminator for efficient transcription termination. They were incorporated into plasmid vectors able to replicate and to be selected in yeast. All of these features were provided by plasmid vectors pDP314, pDP315 and pDP316—see FIG. 18 (C.Hadfield, 1994, In: The Molecular Genetics of Yeast—A Practical Approach, J. R. Johnston (ed), IRL Press, pp. 1748). These plasmids enabled fuision to the Mfα1 secretion leader in three variations, as shown in FIG. 19. Fusion into pDP316 is to the pre peptide which incorporates the secretion signal peptide. Cleavage by signal peptidase at the pre-Ins junction liberates the Ins precursor with a mature B-chain amino-terminus. Fusion into pDP315 provides a pre-pro leader. Cleavage by KEX2 endopeptidase at the pro-Ins junction liberates the Ins precursor with a mature B-chain amino-terminus. Plasmid pDP314 provided fusion to pre-pro-EAEA (where E is Glu and A is Ala). Cleavage by KEX2 endopeptidase liberates EAEA-Ins. Removal of EAEA from the amino-terminus of the Ins precursor by the STE13 exopeptidase is known to be inefficient (Brake, A. J., et al., 1984, Proc. Natl. Acad. Sci. USA, 81: 4642–4646; Thim, L., et al., 1986, supra) and so only a small proportion of the Ins products would be expected to be produced with the mature B-chain amino-terminus.

These leader peptide fusion variants were made to investigate their effect on yield and processing. Evidence indicates that presence of the pro sequence is beneficial to secreted yield in the case of small peptides (Hadfield, C., et al., 1993, Mycol. Res. 97: 897–944). On the other hand, presence of the pro sequence introduces an additional KEX2 processing site, which may be disadvantageous when other KEX2 processing sites occur within the Ins precursor.

Recombinant plasmids were constructed as described (C.Hadfield, 1994, supra). They were recovered by transformation into *E. coli* and DNA preparations isolated.

3. Transformation of *S. cerevisiae* by the Recombinant Plasmids

The pDP vectors contain the ORI-STB region of 2 μm, facilitating multicopy replication and stable inheritance in yeast, and the LEU2 gene, which enables the presence of the plasmid to be selected for in leu2-defective host strains. Plasmid DNA was transformed into yeast by the lithium acetate procedure (Ito, H., et al., 1983, J. Bacteriol. 153: 163–168) and transformants able to grow in minimal medium lacking leucine isolated.

A number of yeast strains were transformed. All were mating-type α to enable the MFα promoter on the plasmid to function. The stains were:

BF307–10 α leu2 trp1 his3 ura3 met4 ade4 ade6 arg4;

DBY746 α leu2 trp1 his3 ura3 can1;

JRY188 α ura3-52 leu2-3,-112 trp1 his4 rme $sir_{ts}$;

PMY1 α leu2-3,-112 his4;

BJ1991 α ura3-52 leu2-3,-112 trp1 pep4-3 prb1-1122; and BF307- 10 kex2:: URA3

These facilitated study of the effect of strain variation and defects in major vacuolar protease encoding genes and the KEX2 endoprotease.

4. Expression and Stability of Recombinant Insulin Genes in Yeast Stability of Ins Plasmids Transformant yeast colonies were inoculated into 10 ml of minimal medium lacking leucine (to maintain the selection for the plasmid) and shaken at 30° C. overnight. Cells from the resultant culture were used to inoculate YPD rich non-selective medium and selective minimal medium. After growth for at least 10 cell doublings, cells were plated to determine the proportion of plasmid-containing cells. In both cases, over 99% of cells contained the plasmid, demonstrating a high degree of mitotic stability and demonstrating that expression of the insulin precursor products did not affect plasmid stability.

Relative Expression Yields

Studies were undertaken to compare the relative yields of insulin precursor products obtained with the different types of constructs. Transformed yeast cells were grown under identical conditions in selective minimal medium or rich YPD medium and the amount of insulin material secreted into the culture medium quantified using the Boehringer ELISA assay kit for insulin, which utilises monoclonal antibodies to both the A- and B-chains of human insulin.

Ins1, Ins2, Ins2–16, Ins3, Ins4 and Ins5 gave very similar yields. The yield for Ins6 was 60% of their level and Ins7 30%, although these may be due to reduced reactivity in the assay rather than less material present. As both Ins1 and Ins2–16 are not cleaved internally by KEX2, the presence of single or double KEX2 sites within the other precursors did not result in reduced yield. These results indicate that precursors internally cleaved by KEX2 endonuclease in yeast may be produced without detriment to yield which would have prevented their economic use for insulin manufacture. Thus, Ins3, which has two internal KEX2 cleavage sites, was not recovered at low yield like other human proinsulin variants expressed from similar construct in yeast (Thim, L. et al., 1986, supra) and so overcomes the inefficiency associated with proinsulin expression in yeast. The other two construct types, having single KEX2 sites either at the junction with the A-chain (Ins2, Ins5) or the B-chain (Ins4, Ins6, Ins7), as indicated in Table 1, showed no significant effect on yield of having a KEX2 site in either of these positions.

Products expressed from pDP314 fusions appeared to form aggregates. This was absent in constructs lacking the amino-terminal GluAlaGluAla peptide extension on the Ins product. Yields were reduced to 25% when fused to the pre sequence alone in pDP3 16, indicating that absence of the pro-sequence reduced yield. Presence of the additional KEX2 site in the pro leader did not seem to affect yield.

Effect of Host Strain and Culture Temperature

The relative maximum yields of Ins products after growth in YPD medium at 30° C. (18–30 hours) were analysed when different yeast host strains were used. Slight but not substantial—variation between strains was observed and mutations in vacuolar protease genes did not influence the yield.

Lowering the culture temperature from 30° C. to 20° C. resulted in an approximately ten-fold increase in yield. An intermediate level was obtained at 25° C. Reduced temperature culture at 20° C., down from the temperature of 30° C. at which S. cerevisiae is commonly incubated, is therefore an important part of the present invention.

Effect of Culture Medium

Insulin precursor product yields were up to 3-fold higher in rich YPD medium than in semi-defined minimal medium. This reflected a difference in cell density rather than a difference in product yield per cell. YPD contains many proteins which are disadvantageous for purification. However, semi-defined minimal medium supplemented with casamino acids, or malt extract medium supplemented with casamino acids, resulted in cell densities and product yields almost as high as YPD medium.

5. Product Characterization

The insulin precursor products secreted by transformed yeasts were characterized by several means.

(a) ELISA assays on culture supernatants using the Boehringer Enzymum-Test Insulin assay kit (catalogue number 1 289 101) detected insulin material in the culture supernatants. The kit utilises two monoclonal antibodies, which recognize B-chain and A-chain eptitopes of human insulin. Further antibody assays were performed at the Department of Clinical Biochemistry, Addenbrookes Hospital, University of Cambridge, with a battery of individual monoclonal antibodies recognizing B-chain or A-chain epitopes. These all reacted with the Ins materials confirming they carried human insulin epitopes.

(b) Culture supernatants were concentrated by a variety of methods—including ultrafiltration. ammonium sulphate precipitation and lyophilization—and samples analysed on both denaturing and non-denaturing polyacrylamide gels for confirmation of the expected molecular weight. Such gels were also western blotted and probed with anti-insulin antibodies. The antibodies used were polyclonal antibodies raised against human insulin in guinea pigs and commercially available monoclonal antibodies for human insulin raised in mouse. Positive reactions against the Ins products were obtained, confirming them to have insulin epitopes.

(c) Loss of the 'C' region of Ins3 (which contains the 9E10 epitope) by endoproteolytic processing was confirmed by probing the western blot with anti-9E10 monoclonal antibody (raised in mouse). In contrast, Ins2 and Ins4, which also contain the 'C' region 9E10 epitope, but which are cleaved only once internally, were recognised by the anti-9E10 antibody.

(d) Chemical verification of the product was obtained by peptide sequencing.

5. Recovery and Purification Via a Specific Affinity Binding Peptide within the 'C Region'.

Insulin precursor products (Ins5, Ins6, Ins7, Ins9 and Ins 10) containing the peptide sequence 'Pur' within the C region may be specifically isolated from the cell-free culture supernatant by affinity column binding (European patent application number 91308382.0). Binding occurs to heparin-sepharose or phosvitin-sepharose. As this system specifically targets an artificial peptide within the C region, it differs from the use of anti-insulin immunoadsorbtion columns, which specifically bind the B- and/or A-chains of insulin (see for example EP-A-0427296).

The Pur peptide is a consensus sequence, derived from studies (at VMSRF) of the interaction of a number of proteins with phosvitin and heparin. The Pur peptide provides predominantly basic charges that are required for such interaction. In addition, it has been designed to avoid internal cleavage by KEX2 endopeptidase, so that it remains intact during passage through the yeast secretion pathway.

6. Production of Mature Insulin (a) From Insulin Precursor Type I

A precursor of the type B-KR-X-KR-A directed into the yeast secretion pathway, where it folds and the disulphide bonds form, may be fully cleaved by KEX2 to yield the product A::B-KR, in which :: represents the two disulphide bonds established between the A- and B-chains.

Complete in vivo exonuclease modification by KEX1 will remove the KR residues (Dmochowska, A., et al., 1987, Cell 50: 573–584) to produce mature insulin, A::B.

Inefficient processing by KEX2 may result in single cleavage products (A::B-KR-X-KR or X-KR-A::B-KR) or uncleaved product,

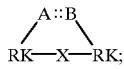

being secreted into the culture medium. To increase the yield, these may be treated in vitro with trypsin to cleave at the KR residues (W. Kemmler et al., 1971, J. Biol. Chem. 246 6786–6791).

By similar token, inefficient in vivo processing by KEX1 may be compensated by in vitro treatment with carboxypeptidase B.

In the case of Ins3, an example of this kind of precursor, analysis of the secretion products from yeast indicates the presence of mature insulin and some higher molecular weight precursors.

(b) From Precursor Types II. III. IV and V

Precursors having the general formula (II): B-KR-X-M-A are cleaved in vivo by KEX2 and secreted by yeast in the form: X-M-A::B(-KR) where (-KR) indicates that these residues may be removed by KEX1 activity in vivo or by carboxypeptidase B in vitro. Treatment with cyanogen bromide cleaves at the M residue to produce mature insulin.

The advantage of this kind of insulin derivation is most apparent with precursors derived from the general formula (II), having the general formula (III): B-KR-Pur-M-A and its derivative having the general formula (V): B-KR-Y-N-Pur-M-A (V). These contain an affinity purification sequence (Pur) within the 'C region', which enables the precursor to be recovered, purified and concentrated from the culture supernatant. Subsequent cleavage with cyanogen bromide removes this purification sequence and it may be separated from the mature insulin product by passage through an affinity column, on which it will be retained.

(c) From Precursor Type VI

Precursors having the general formula (VI): B-N-X-KR-A are cleaved in vivo by KEX2 and secreted by yeast in the form: A::B-N-X(-KR) where (-KR) indicates that these residues may be removed by KEX1 activity in vivo or by carboxypeptidase B in vitro. If N is aspartic acid, in vitro treatment with *P. fragi* mutant Me1 endopeptidase (Sigma Catalogue No. P3303 Me1 endopeptidase from mutant *Pseudomonas fragi*) cleaves amino-terminally to the N residue to produce mature insulin.

Derivatives containing an affinity purification sequence (Pur) within X can be recovered, purified and concentrated from the culture supernatant. Subsequent cleavage at N removes this purification sequence and it may be separated from the mature insulin product by passage through an affinity column, on which it will be retained.

7. Second Products

Precursors having the general formula (V): B-KR-Y-N-Pur-M-A or its derivatives, or analogous derivatives of formula (VI), incorporate a second product within the 'C region'. These are separated from the insulin product by cyanogen bromide treatment as in 6(b) above.

EXPERIMENTAL

General molecular biology and recombinant DNA methods used throughout the experimental work are as described in J. Sambrook et al., 1989, *Molecular cloning: A laboratory manual*, 2nd edition, Cold Spring Harbor Laboratory, New York; and G. J. Boulnois, 1987, *Gene cloning and analysis, a laboratory guide*, Blackwell Scientific Publications, Oxford.

Example 1

Construction of Synthetic Recombinant Insulin Precursor Sequences (a) Oligonucleotide Synthesis.

The synthetic insulin precursor encoding sequences were designed to use only codons that are highly expressed in *S. cerevisiae* and be constructed using chemically synthesised oligonucleotides. Six oligonucleotides (incorporating A chain, B chain and modified C chain) were chemically synthesised on Applied Biosystem DNA synthesiser at the Department of Biochemistry and Pathology, University of Cambridge, Cambridge, England. The sequences and sizes were:

Oligo A1 (SEQ ID NO: 19; 92mer)
  5' CTA CAC TCC AAA GAC TAA GAG AGG TAT CGT TGA ACA ATG TTG TAC TTC TAT CTG TTC TTT GTA CCA ATT GGA AAA CTA CTG TAA CTA ATA AG 3'

Oligo A2 (SEQ ID NO: 20: 80mer)
  5' GAT CCT TAT TAG TTA CAG TAG TTT TCC AAT TGG TAC AAA GAA CAG ATA GAA GTA CAA CAT TCT TCA ACG ATA CCT CTC TT 3'

Oligo B1 (SEQ ID NO: 21: 78mer)
  5' AGC TTT CGT TAA CCA ACA CTT GTG TGG TTC TCA CTT GGT TGA AGC CTT GTA CTT GGT TTG TGG TGA AAG AGG TTT CTT 3'

Oligo B2 (SEQ ID NO: 22: 90mer)
  5' ACT CTT TGG AGT GTA GAA GAA ACC TCT TTC ACC ACA AAC CAA GTA CAA GGC TTC AAC CAA GTG AGA ACC ACA CAA GTC TTG GTT AAC GAA 3'

Oligo B3 (SEQ ID NO: 23: 134mer)
5' CTA CAC TCC AAA GAC TAT GCA TGA ACA AAA GTT GAT CTC TGA AGA AGA CTT GGT CGA CAA GAG AGG TAT GCT TGA ACA ATG TTG TAC TTC TAT CTG TTC TTT GTA CCA ATT GGA AAA CTA CTG TAA CTA ATA AG 3'

Oligo B4 (SEQ ID NO: 24: 122mer)
5' GAT CCT TAT TAG TTA CAG TAG TTT TCC AAT TGG TAC AAA GAA CAG ATA GAA GTA CAA CAT TGT TCA ACG ATA CCT CTC TTG TCG ACC AAG TCT TCT TCA GAG ATC AAC TTT TGT TCA TGC AT 3'

The yields (1 unit $A_{260}$=33 μg/ml) of these oligonucleotides on 0.2 mmole scale were: Oligo A1 137 units, Oligo A2 89 units, Oligo B1 93 units, Oligo B2 113 units, Oligo B3 128 units and Oligo B4 108 units, respectively. Their integrity was checked by running the $^{32}$P end-labelled samples of the oligonucleotide preparations on denaturating polyacrylamide gels and visualising the size-separated products by autoradiography.

(b) Purification of Oligonucleotides and Phosphorylation

The oligonucleotides synthesised above were ethanol precipitated and pelleted in a microcentrifuge. The oligonucleotide pellets were suspended in water (distilled and deionized) and then aliquots electrophoresed in a preparative denturating polyacrylaminde gel. The size-separated DNA was visualized by UV shadowing and the top-most band (i.e. the largest sized oligonucleotide) in each case excised from the gel with a sterile scalpel blade. The DNA was eluted with elution buffer (0.5 M NH40AC, 1 mM EDTA [pH 8.0]) at room temperature (24° C.) for 16 hours. The eluted DNA was again ethanol precipitated, dried and suspended in water. The gel purified DNAs were phosphorylated (5'-OH end) using polynucleotide kinase.

(c) Construction of Ins1

1. Annealing of Oligonucleotides and Cloning of Duplex DNA

Purified oligonucleotides A1 and A2 were mixed together, each at a concentration of 1 mg/ml in water, and sealed within a glass capillary. Purified oligonucleotides B1 and B2 were likewise mixed together. One litre of water was heated to 100° C. and the heat source turned off. The two capillaries containing the oligonucleotides were immersed in the boiling water bath, which was then covered with aluminium foil and allowed to cool slowly overnight to room temperature.

The two glass capillaries were opened and the contents mixed together. The mixture was then immersed in an 80° C. water bath, which was allowed to cool to room temperature.

The annealed duplex DNA was cloned into pUC19 that had been cleaved with HindIII and BamH1. The ligation reaction not only joined the synthetic DNA into the vector, but also simultaneously joined the backbones of A1–A2 to B1–B2 (see FIG. 1).

2. Recovery of Clones and Initial Analysis

The ligated DNA was transformed into competent cells of *E. coli* strain NM522 (supE thi (lac-proAB)$^\Delta$hsd$^\Delta$5(rk$^{31}$mk$^+$), [F' proAB lacI$^Q$Z$^\Delta$M15]) and plated onto L agar containing ampicillin (50 μg/ml) and X-gal (25 μg/ml).

White recombinant colonies (non-recombinants blue) were picked and cultured in L broth containing ampicillin at 37° C. for 16 hours. Plasmid DNA was then extracted using the alkaline lysis method (Birnboim and Doly).

The plasmid DNAs were restricted with HindIII and BamHI and the presence of a 170 bp band (cloned synthetic DNA) looked for by gel electrophoresis.

3. Purified Plasmid DNA Preparation and DNA Sequence Analysis

Purified plasmid preparations were made using triton lysis followed by ethidium bromide/caesium chloride density gradient ultracentrifugation. The plasmid DNA was quantified ($A_{260}$) and re-analysed by gel electrophoresis.

The cloned synthetic DNAs were sequenced using the T7 sequencing kit from Pharmacia and employed the M13 mp universal primers. The sequence shown in FIG. 2 was verified.

(d) Construction of Ins2

1. Annealing of Oligonucleotides and Cloning of Duplex DNA

Purified oligonucleotides A3 and A4 were mixed together, each at a concentration of 1 mg/ml in water, and sealed within a glass capillary. Purified oligonucleotides B1 and B2 were likewise mixed together. One litre of water was heated to 100° C. and the heat source turned off. The two capillaries containing the oligonucleotides were immersed in the boiling water bath, which was then covered with aluminium foil and allowed to cool slowly overnight to room temperature.

The two glass capillaries were opened and the contents mixed together. The mixture was then immersed in a 80° C. water bath, which was allowed to cool to room temperature.

The annealed duplex DNA was cloned into pUC19 that had been cleaved with HindIII and BamHI. The ligation reaction not only joined the synthetic DNA into the vector, but also simultaneously joined the backbones of A3–-A4 to B1–B2 (see FIG. 3).

2. Recovery of Clones and Initial Analysis

The ligated DNA was transformed into competent cells of *E. coli* strain NM522 (supE thi (lac-proAB)$^\Delta$hsd$^\Delta$5(rk$^-$mk$^+$), [F' proAB lacI$^Q$Z$^\Delta$M15])D and plated onto L agar containing ampicillin (50 μg/ml) and X-gal (25 μg/ml).

White recombinant colonies (non-recombinants blue) were picked and cultured in L broth containing ampicillin at 37° C. for 16 hours. Plasmid DNA was then extracted using the alkaline lysis method (Bimboim and Doly).

The plasmid DNAs were restricted with HindIII and BamH1 and the presence of a 212 bp band (cloned synthetic DNA) looked for by gel electrophoresis. Clones showing such a band were further analysed on restriction digestion gels to verify the presence of NsiI and SalI sites within the cloned DNA.

3. Purified Plasmid DNA Preparation and DNA Sequence Analysis

Purified plasmid preparations were made using triton lysis followed by, ethidium bromide/caesium chloride density gradient ultracentrifugation. The plasmid DNA was quantified ($A_{260}$) and re-analysed by gel electrophoresis.

The cloned synthetic DNAs were sequenced using the T7 sequencing kit from Pharmacia and employed the M13 mp universal primers.

4. Final Derivation of Ins2 Via In Vitro Recombination

Figure 4:
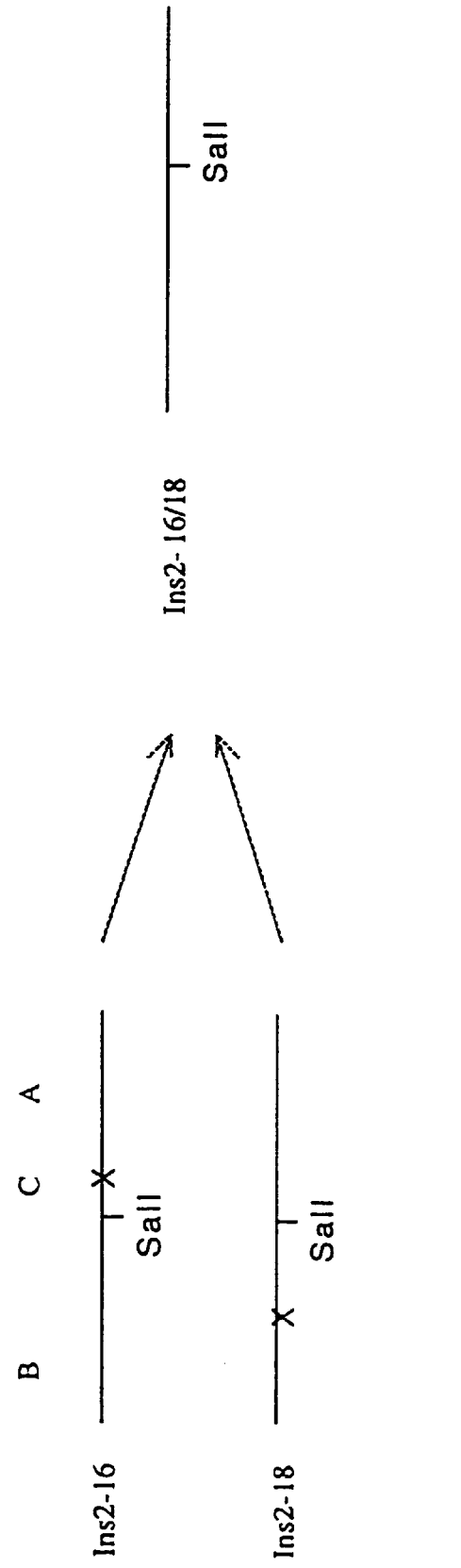
FIG. 4 illustrates the final derivation of Ins2 via in vitro recombination of two precursors containing errors. Ins2–16 has 1 base missing in the C region Lys-Arg. Ins2–18 has an error in the B-chain. Ins2–16/18 is constructed by in vitro recombination at the SalI site of the sequence correct Ins2–16 'B arm' with the Ins2–18 sequence correct 'A arm'.

All of the synthetic cloned DNAs analysed by sequencing contained mutations of the desired sequence. In order to obtain an Ins2 clone of the required sequence, two defective versions—Ins2–16 and Ins2–18—were used to create an in vitro recombined correct version, Ins2–16/18. This was possible because the defects in clones 16 and 18 were on opposite sides of the central SalI site, as indicated in the FIG. 4.

The HindIII-SalI fragment from Ins2–16, and the SalI-BamHI fragment from Ins2–18, were isolated from preparative polyacrylamide gels and ligated together into pUC19 to create Ins2–16/18. The authenticity of this clone was verified by sequencing (see FIG. 5).

(e) Construction of Ins3

Ins3 was derived from Ins2 using PCR mutagenesis, the strategy for which is shown in FIG. 6. The primers used to change MetHis codons to LysArg are shown in FIG. 7. Clones obtained were sequenced to confirm they would encode the product shown in FIG. 8 when expressed in yeast.

(f) Construction of Ins4

Ins4 was derived from Ins3 using the PCR mutagenesis strategy described in FIG. 6. The primers used to change an Arg codon to Met are shown in FIG. 7. Clones obtained were sequenced to confirm they would encode the product shown in FIG. 9 when expressed in yeast.

(g) Construction of Ins5

Figure 10:
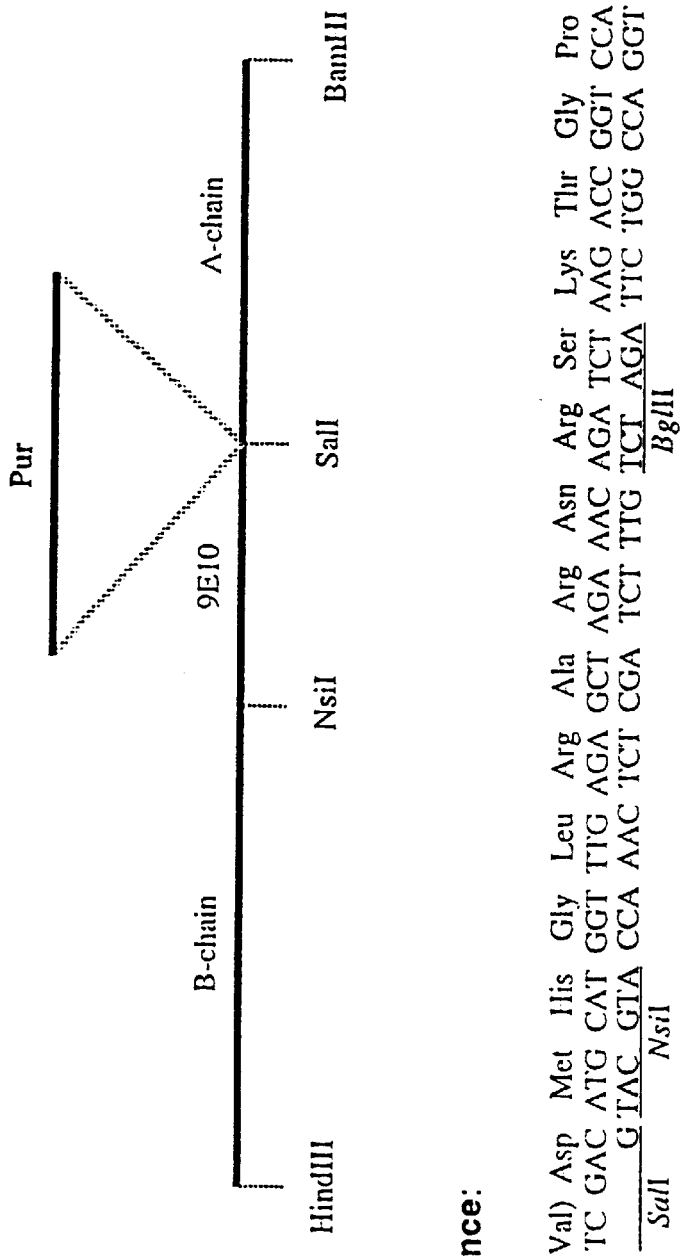
FIG. 10 illustrates the derivation of Ins5 from Ins2 via insertion of a double-stranded synthetic oligonucleotide (Pur) into the SalI site. The Pur sequences form part of SEQ ID NOs: 6 and 13 (Ins5)

Ins5 was created by inserting a synthetic purification sequence (Pur) into the SalI site of Ins2 (FIG. 10). The Pur sequence—as shown in FIG. 10—was created by annealing two synthetic oligonucleotides (prepared as described for Ins1 and Ins2 construction above). Clones obtained were sequenced to confirm they would encode the product shown in FIG. 11 when expressed in yeast.

(h) Construction of Ins6

Figure 12:
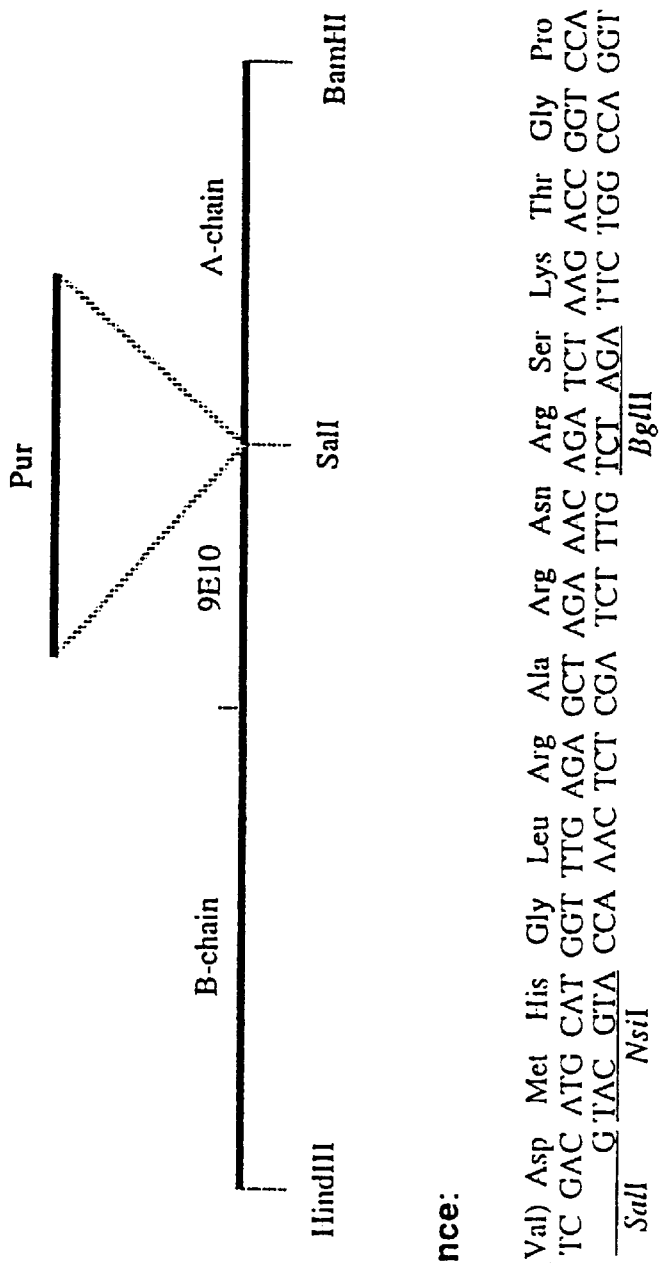
FIG. 12 illustrates the derivation of Ins6 from Ins4 via insertion of a double-stranded synthetic oligonucleotide (Pur) into the SalI site. The Pur sequence is residues 43–60 of SEQ ID NO: 3 and corresponding nucleotides of SEQ ID NO: 14.

Ins6 was created by inserting the synthetic purification sequence, Pur, into the SalI site of Ins4 (FIG. 12). Clones obtained were sequenced to confirm they would encode the product shown in FIG. 13 when expressed in yeast.

(i) Construction of Ins7

Figure 14:
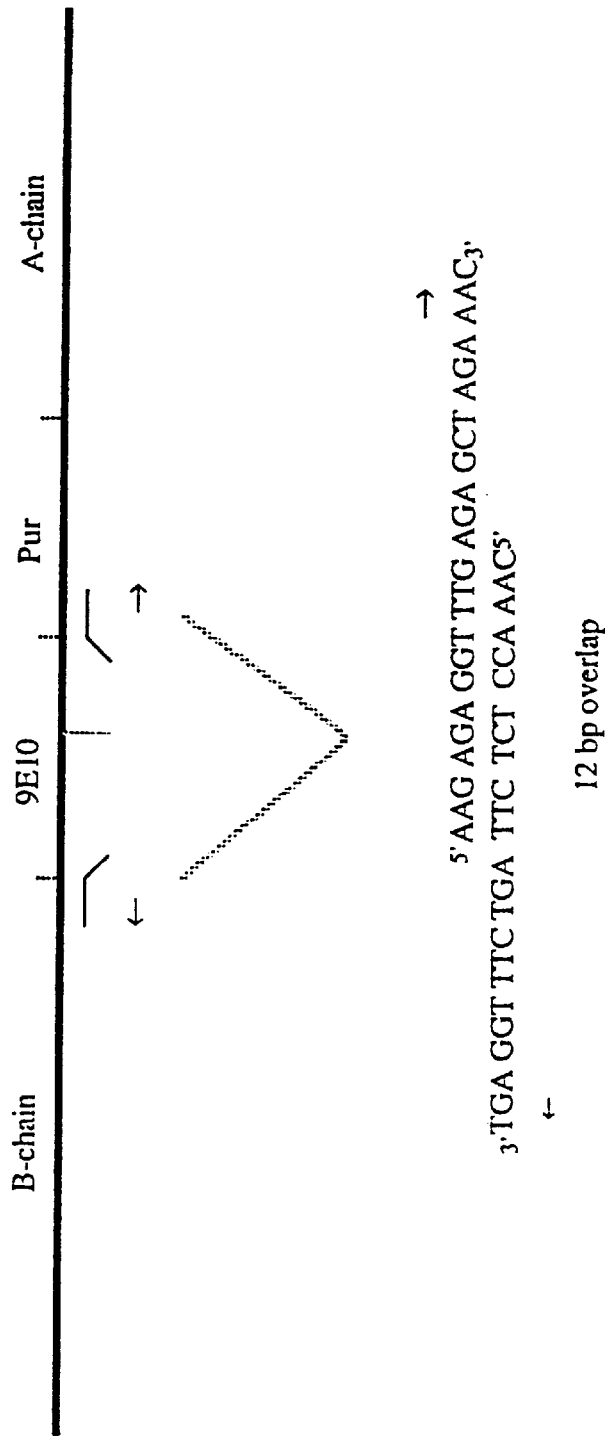
FIG. 14 illustrates the general strategy for the derivation of Ins7 from Ins6 via PCR deletion of the 9E 10 sequence with overlapping primers having SEQ ID NOs: 32 and 33.

Ins7 was derived from Ins6 by PCR deletion using the general strategy of FIG. 6 as shown in FIG. 14. Clones obtained were verified by sequencing (FIG. 15).

(j) Construction of Ins8

Ins8 was derived from Ins4 by PCR mutagenesis using the general strategy of FIG. 6 as shown in FIG. 16. Clones obtained were sequenced to verify the change of residue $B_{30}$.

(k) Construction of Ins9

Ins9 was derived from Ins6 by PCR mutagenesis using the general strategy of FIG. 6 as shown in FIG. 16. Clones obtained were sequenced to verify the change of residue $B_{30}$.

(l) Construction of Ins10

Ins10 was derived from Ins9 by PCR mutagenesis using the general strategy of FIG. 6 as shown in FIG. 17. Clones obtained were sequenced to verify the change of residues $A_8$ and $A_{10}$.

Example 2

Construction of MFα1—Ins Fusion Shuttle Vector Plasmids pUC19-Ins plasmid DNA (where Ins represents all Ins precursor gene constructs, Ins1 to Ins10) was cleaved with HindIII and BamHI to liberate the Ins fragment DNA. The DNA was size separated by electrophoresis on a 3.5% polyacrylamide gel and stained with ethidium bromide. The Ins DNA fragment was excised under ultraviolet illumination and the DNA eluted and concentrated by ethanol precipitation.

pDP314, pDP315 and pDP316 DNA were cleaved with HindIII and BamHI, phenol-chloroform extracted and then ethanol precipitated and washed with 70% ethanol (Boulnois et al). The pellet was resuspended in 400 μl of TE buffer, ethanol precipitated, washed with 70% ethanol and dried under vacuum.

Ins fragment and pDP vector DNAs were resuspended in 5 mM Tris-HC1 (pH 7.5). To make in vitro recombinant plasmid clones, 1.0 μg of pDP DNA was mixed on ice with 20 ng of Ins fragment DNA, ligation buffer and T4 DNA ligase, in a total volume of 25 μl, and incubated overnight at 15° C. The ligated DNA was transformed into *E. coli* and ampicillin-resistant colonies selected on L agar containing 50 μg/ml ampicillin.

Colonies were picked into L broth containing 50 μml ampicillin and incubated overnight at 37° C. in a shaking incubator. Plasmid DNA was extracted and analysed for the presence of the correctly sized pDP vector and Ins insert fragments following digestion with HindIII and BamHI. In the cases of Ins2–10, their presence could be detected by introduction of SalI or NsiI sites.

Insertion of the HindIII-BamHI Ins fragments into pDP314 resulted in creation of the required fusion with the MFα pre-pro-EAEA leader (as shown in FIG. 19). In the cases of pDP315 and pDP316 further modifications had to be made to generate the required fusions. In the case of pDP315-Ins the first step was cleavage of 2.5 μg of the DNA with HindIII and StuI, followed by phenol-chloroform extraction, ethanol precipitation, washing with 70% ethanol and vacuum drying. The 5' single-stranded projection at the HindIII end was removed by treatment with mung bean exonuclease (Pharmnacia). Afterwards, the enzyme was denatured by phenol-chloroform extraction, followed by ethanol precipitation, washing with 70% ethanol and vacuum drying. The DNA was resuspended in 5 mM Tris-HCI (pH 7.5) and recircularized by ligation. This process removed the EAEA dipeptides, creating a pre-pro-Ins fusion (as shown in FIG. 19).

In the case of pDP316-Ins the first step was cleavage of 2.5 μg of the DNA with HindIII and SphI, followed by phenol-chloroform extraction, ethanol precipitation, washing with 70% ethanol and vacuum drying. The 5' single-stranded projection at the HindIII end and the 3' projection at the SphI end were removed by treatment with mung bean exonuclease (Pharmacia). Afterwards the enzyme was denatured by phenol chloroform extraction, followed by ethanol precipitation, washing with 70% ethanol and vacuum drying. The DNA was resuspended in 5 mM Tris-HCI (pH 7.5) and recircularized by ligation. This process removed the pro-peptide and EAEA dipeptides, creating a pre-Ins fusion (as shown in FIG. 19).

All fusions were sequence verified using the following primers:

```
314/315 (-40)        AAA TAC TAC TAT TGC CAG C
(SEQ ID NO: 25)

or 316 (-64)            CAT ACA CAA TAT AAA CGA CC
(SEQ ID NO: 26)

with ADH reverse (-44) CAA GGT AGA CAA GCC GAC
(SEQ ID NO: 27)
```

Example 3

Expression in Yeast

Insulin precursor products secreted in the culture medium by transformant cells carrying the different synthetic gene constructions were quantified using the Boehringer ELISA assay kit for insulin, which utilises monoclonal antibodies to both the A- and B-chains of human insulin.

Shake-flask cultures were inoculated from a fresh overnight minimal selective culture at 1:1000 dilution and incubated at the prescribed temperature with continuous shaking. Samples were withdrawn periodically for analysis: cell growth was monitored by increase in optical density at 600 nm and insulin yield by ELISA assay. Stationary phase in cell growth was reached after 24–36 hours, depending upon medium, and this coincided with peak insulin yield.

(a) Yields in YPD

Culture at 30° C. of BF307–10 transformants resulted in yields of approximately 2.0 mg/l for Ins1, Ins2, Ins2–16, Ins3, Ins4 and Ins5 fused to the pre-pro leader. Yields calculated by ELISA assay for Ins6 were 1.6 mg/l and 0.8 mg/l for Ins7, although gel analysis suggested this reflected relative reactivity towards the Ins products rather than less material. Products expressed from pDP314 fusions appeared to form aggregates. This was absent in constructs lacking the amino-terminal GluAlaGluAla peptide extension on the Ins product. Yields were reduced to 25% of the above when fused to the pre sequence alone in pDP316, indicating that absence of the pro sequence reduced yield. Presence of the additional KEX2 site in the pro leader did not seem to affect yield.

As Ins 1 and Ins2–16, which were not subject to internal KEX2 proteolytic cleavage, showed similar yields to the other construct forms, the presence of KEX2 cleavage sites within the Ins region did not reduce yield. Thus, Ins3, which has two internal KEX2 cleavage sites, was not recovered at low yield like human proinsulin expressed from a similar construction in yeast (Thim et al., 1986, Proc. Natl. Acad. Sci. USA, 83: 6766–6770) and so overcomes the inefficiency associated with proinsulin expression in yeast.

The other two construct types, having single KEX2 sites either at the junction with the A-chain (Ins2, Ins5) or the B-chain (Ins4, Ins6, Ins7), as indicated in Table 1, showed no effect on yield of having a KEX2 site in either of these positions.

(b) Effect of Host Strain

The relative maximum yields of Ins products after growth in YPD medium at 30° C. (18 30 hours) were analysed the cells were removed and ELISA assays for insulin.

| | $A_{420}$ nm* | | |
|---|---|---|---|
| Strain | Ins7 | Ins6 | Ins1 |
| BF307-10 | | | 1.75 |
| PMY1 | 1.14 | 1.33 | |
| DBY746 | 0.58 | | |
| BJ1991 | 0.87 | | 0.90 |
| TGY47.1 | | | 1.47 |

*Unconverted data from ELISA assay.

Thus, there is a slight effect of yeast host strain on yield, but not a substantial one.

(c) Effect of Culture Temperature on Yield

Lowering the culture temperature from 30° C. to 20° C. resulted in a yield of 15–20 mg/l in YPD—a ten-fold increase over the yield at 30° C. An intermediate level was obtained at 25° C.

(d) Yields in Other Media

PMY1 transformant cells were inoculated into different media (all containing 2% glucose) from a minimal selective culture, as described, and shaken at 30° C. for 24 hours. Cell growth was measured by absorbance at 600 nm and the amount of insulin product in the culture medium determined ($A420$ nm being the unconverted ELISA data). The data shown are for the Ins7 and Ins6 products.

| | Ins7 | | | Ins6 | | |
|---|---|---|---|---|---|---|
| | Cell $A_{600}$ | Ins $A_{420}$ | Ins cell | Cell $A_{600}$ | Ins $A_{420}$ | Ins cell |
| YPD | 7.10 | 1.03 | 0.14 | 7.32 | 1.22 | 0.17 |
| ME | 4.80 | 0.47 | 0.10 | 4.70 | 1.00 | 0.21 |
| ME + CA | 6.18 | 0.72 | 0.12 | 7.06 | 0.99 | 0.14 |
| SD | 2.40 | 0.39 | 0.16 | 2.10 | 0.90 | 0.43 |
| SD + CA | 6.63 | 0.83 | 0.12 | 5.50 | 1.12 | 0.20 |

ME = 2% malt extract; CA = 1% casamino acids; SD = semi-defined minimal medium

The results show that although cell growth varied quite widely between different media, insulin product yield per unit cell OD remained fairly constant.

Example 4

Characterization of the Ins3 Product

A sample of the Ins3 product was concentrated by ultrafiltration, using the Millipore minitan system with a filter having a 3,000 Dalton molecular weight cut-off. The retentate was then passed through a 30,000 Dalton molecular weight cut-off Centricon filter to remove proteins of $\geq 30,000$ Daltons. The sample was further purified by gel filtration on a Sephadex GSOM column. Peak fractions containing insulin activity were then run on a preparative SDS-polyacrylamide gel. After blotting onto a membrane, the slower-running band was peptide sequenced by the Leicester University peptide sequencing service. The product obtained had the same peptide sequence as human insulin B-chain (Table 2). When pDP314 was used as the vector the major product contained GluAlaGluAla at the amino-terminus, showing failure to be removed by the STE13 exopeptidase. As anticipated from the work of A. J. Brake et al., 1984, supra and Thim, L., et al., 1986, spra, the pDP314 product is unsuitable for pharmaceutical use. However, products in which the amino-terminus is derived by endopeptidase cleavage, such as from the pDP315 and pDP316, provide the correct aminoterminus for the B-chain and are therefore suitable for pharmaceutical use.

Example 5

Recovery and Purification Via a Specific Affinity Binding Peptide within the 'C Region'

The Ins5, Ins6, Ins7, Ins9 and Ins10 products contain a peptide sequence 'Pur' within the C region that enables affinity purification (see for example EP-A-91308382.0).

(a) Column Preparation 40 ml of heparin-sepharose or phosvitin-sepharose gel was packed onto a sintered glass column (60 mm diam.×100 mm length). The gel bed thickness was 12–16 mm.

(b) Affinity Binding and Recovery

BJ 1991 (pDP314-Ins2), BJ1991 (pDP3 14-lns6) and BJ1991 (pDP314-Ins7) transformant cells were cultured in YPD medium for 24 hours at 30° C. 100 ml of culture supematant was adjusted to pH 7.5. Heparin-sepharose columns were equilibrated with 20 mM TrisHCl pH 7.5 and the supematants loaded

| | Proportion of Ins material binding | | | |
|---|---|---|---|---|
| | column 1 | | column 2 | Elution of |
| | pass 1 | pass 2 | pass 3 | bound material |
| Ins2 | none | none | none | |
| Ins6 | 50% | 12% | none | 100% |
| Ins7 | 40% | 10% | none | 100% |

Only Ins material containing the Pur sequence (Ins6 and Ins7, not Ins2) binds to the column. The Pur sequence therefore facilitates purification.

Reloading of the breakthrough of the first pass through the column results in more material binding. However, loading of the breakthrough of the second pass onto a fresh column did not result in more binding. Thus, 40–50% of the material failed to bind under these conditions.

Elution with 20 mM Tris-HCl pH 7.5, 1.0 M NaCl resulted in recovery of all the material that had bound to the column.

Similar results were obtained with phosvitin-sepharose as the column material.

Improved binding efficiency was obtained using altered binding buffer conditions. The heparin-sepharose column was equilibrated with 20 column volumes of sodium acetate buffer pH 5.0. The Ins7 culture supernatant was adjusted to pH 4.5–5.0 with glacial acetic acid and loaded onto the column under gravity. The column was washed with 20 mM sodium phosphate buffer pH 6.25 after loading to recover unbound material.

| | $A_{420}$ units | % of input |
|---|---|---|
| Input activity (from 1.21 culture) | 1,018,200 | 100% |
| Passed through column in loading 1 | 60,000 | 6% |

-continued

| | $A_{420}$ units | % of input |
|---|---|---|
| Passed through column in loading 2 | 20,000 | 2% |
| Totalbound | 998,200 | 98% |

Elution with 250 ml of 20 mM sodium phosphate buffer pH 6.25, 0.5 M NaCl resulted in recovery of all of the bound material.

The 2% of material that failed to bind to the column was aggregated material associated with the pDP314 fusion construction.

TABLE 1

RECOMBINANT INSULIN PRECURSOR VARIANTS

| | | | | Tag | |
|---|---|---|---|---|---|
| Construct | Structure | Chains | Extension | Processing | Purification |
| Ins1 | B--KR--A | 1 | | | |
| Ins2 | B--M-9E10-KR--A | 2 | (B-chain)-C | + | |
| Ins2–16 | B--M-9E10-R--A | 1 | | + | |
| Ins3 | B--KR-9E10-KR--A | 2 | | + | |
| Ins4 | B--KR-9E10-KM--A | 2 | N-(A-chain) | + | |
| Ins5 | B--MH-9E10-Pur-KR--A | 2 | (B-chain)-C | + | + |
| Ins6 | B--KR-9E10-Pur-KM--A | 2 | N-(A-chain) | + | + |
| Ins7 | B--KR-Pur-KM--A | 2 | N-(A-chain) | | + |
| Ins8 | B(Ala$^{30}$)--KR-9E10-KM--A | 2 | N-(A-chain) | + | |
| Ins9 | B(Ala$^{30}$)--KR-9E10-Pur-KM--A | 2 | N-(A-chain) | + | + |
| Ins10 | B(Ala$^{30}$)--KR-9E10-Pur-KM--A(Ala$^8$, Ile$^{10}$) | 2 | N-(A-chain) | + | + |

What is claimed is:

1. A DNA sequence encoding a protein precursor of insulin, wherein the precursor has a formula selected from any one of the group of SEQ ID NOs: 1 to 6.

2. A DNA sequence encoding a protein precursor of insulin, wherein the precursor has a formula selected from any one of the group of SEQ ID NOs: 7, 8 and 9.

3. A DNA sequence encoding a single-chain protein precursor wherein the precursor has a formula selected from the group consisting of SEQ ID NOs 1 to 9.

4. A DNA sequence selected from the group consisting of SEQ ID NOs: 10 to 18, or a DNA sequence that encodes the same protein as encoded by any one of SEQ ID NOs: 10 to 18.

5. A yeast or fungal cell transfected or transformed with a DNA sequence selected from any one of the group of SEQ ID NOs: 10 to 18, or a DNA sequence that encodes the same protein as encoded by any one of SEQ ID NOs: 10 to 18.

6. A DNA sequence encoding a single-chain insulin precursor having the formula B-KR-Pur-M-A wherein A and B represent the A and B polypeptide chains, respectively, of insulin, K is lysine, R is arginine, Pur is a purification sequence of amino acid residues that can be recognized and bound by another molecule for in vitro separation of an insulin precursor containing the sequence from a mixture of molecules, and M is methionine, and cleavage at the KR residues produces a double-chain insulin precursor Pur-M-A::B, wherein :: represents two disulfide bonds established between the A and B chains.

7. The DNA sequence according to claim 6 wherein treatment of the double-chain insulin precursor with cyanogen bromide both cleaves off the Pur sequence and simultaneously produces the mature insulin molecule A::B.

8. The DNA sequence according to claim 6 wherein the insulin is selected from the group consisting of human insulin, porcine insulin and bovine insulin.

9. The DNA sequence according to claim 6 wherein the purification sequence binds specifically to heparin and/or phosvitin.

10. A DNA sequence encoding a single-chain insulin precursor having the formula B-KR-Y-M-A wherein A and B represent the A and B polypeptide chains, respectively, of insulin, K is lysine, R is arginine, Y is an additional biological polypeptide of interest, and M is methionine, and cleavage at the KR residues produces a double-chain insulin precursor Y-M-A::B, wherein :: represents two disulfide bonds established between the A and B chains.

11. The DNA sequence according to claim 10 wherein treatment of the double chain insulin precursor with cyanogen bromide produces the mature insulin molecule A::B and releases the polypeptide Y.

12. The DNA sequence according to claim 10 wherein Y is a c-myc peptide sequence.

13. The DNA sequence according to claim 10 wherein the insulin is selected from the group consisting of human insulin, bovine insulin and porcine insulin.

14. A DNA sequence encoding a single-chain insulin precursor having the formula B-KR-Y-N-Pur-M-A, wherein A and B represent the A and B polypeptide chains, respectively, of insulin, K is lysine, R is arginine, Y is an additional biological polypeptide of interest, N is methionine or aspartic acid, Pur is a purification sequence of amino acid residues that can be recognized and bound by another molecule for in vitro separation of an insulin precursor containing the sequence from a mixture of molecules, and M is methionine, and cleavage at the KR residues produces a double-chain insulin precursor Y-N-Pur-M-A::B, wherein :: represents two disulfide bonds established between the A and B chains.

15. The DNA sequence according to claim 14 wherein N is methionine and treatment of the double-chain insulin precursor with cyanogen bromide causes cleavage of the polypeptide Y from the purification sequence.

16. The DNA sequence according to claim 14 wherein N is aspartic acid and treatment of the double-chain insulin precursor with *Pseudomonas fragi* mutant Me1 endopeptidase causes cleavage of the polypeptide Y from the purification sequence.

17. The DNA sequence according to claim 14 wherein Y is a c-myc peptide sequence, and the purification sequence Pur binds specifically to heparin and/or phosvitin.

18. The DNA sequence according to claim 14 wherein the insulin is selected from the group consisting of human insulin, bovine insulin and porcine insulin.

19. A DNA sequence encoding a single-chain insulin precursor having the formula B-N-X-KR-A wherein A and B represent the A and B polypeptide chains, respectively, of insulin, N is methionine or aspartic acid, K is lysine, R is arginine, and X is a chain of amino acid residues sufficient in length to facilitate cleavage in a yeast or fungal host cell at the KR residues, and cleavage at the KR residues produces a double-chain insulin precursor A::B-N-X wherein :: represents two disulfide bonds established between the A and B chains.

20. The DNA sequence according to claim 19 wherein the chain X of amino acid residues comprises a purification sequence Pur and/or an additional biological polypeptide of interest Y, wherein Pur is a sequence of amino acid residues that can be recognized and bound by another molecule for in vitro separation of an insulin precursor containing the sequence from a mixture of molecules.

21. The DNA sequence according to claim 20 wherein Y is a c-myc peptide sequence.

22. The DNA sequence according to claim 20 wherein the purification sequence binds specifically to heparin and/or phosvitin.

23. The DNA sequence according to claim 19 wherein the insulin is selected from the group consisting of human insulin, bovine insulin and porcine insulin.

24. A double-chain insulin precursor having the formula Pur-M-A::B wherein A and B represent the A and B polypeptide chains, respectively, of insulin and :: represents two disulfide bonds established between the A and B chains, M is methionine, and Pur is a purification sequence of amino acid residues that can be recognized and bound by another molecule for in vitro separation of the insulin precursor from a mixture of molecules.

25. The double-chain insulin precursor according to claim 24 wherein the double-chain precursor is secreted by a yeast or fungus host cell transformed by a recombinant DNA coding for a single-chain precursor of the double-chain insulin precursor and a leader peptide.

26. The double-chain insulin precusor according to claim 25 wherein the single-chain precursor has the formula B-KR-Pur-M-A, wherein K is lysine and R is arginine.

27. The double-chain insulin precursor according to claim 24 wherein the insulin is selected from the group consisting of human insulin, porcine insulin and bovine insulin.

28. A double-chain insulin precursor having the formula Y-M-A::B wherein A and B represent the A and B polypeptide chains, respectively, of insulin and :: represents two disulfide bonds established between the A and B chains, M is methionine, and Y is an additional polypeptide of interest.

29. The double-chain insulin precursor according to claim 28 wherein the double-chain precursor is secreted by a yeast or fungus host cell transformed by a recombinant DNA coding for a single-chain precursor of the double-chain insulin precursor and a leader peptide.

30. The double-chain insulin precursor according to claim 29 wherein the single-chain precursor has the formula B-KR-Y-M-A, K is lysine and R is arginine.

31. The double-chain insulin precursor according to claim 28 wherein the insulin is selected from the group consisting of human insulin, porcine insulin and bovine insulin.

32. A double-chain insulin precursor having the formula Y-N-Pur-M-A::B wherein A and B represent the A and B polypeptide chains, respectively, of insulin and :: represents two disulfide bonds established between the A and B chains, M is methionine, N is methionine or aspartic acid, Y is an additional polypeptide of interest, and Pur is a purification sequence of amino acid residues that can be recognized and bound by another molecule for in vitro separation of the insulin precursor from a mixture of molecules.

33. The double-chain insulin precursor according to claim 32 wherein the double-chain precursor is secreted by a yeast or fungus host cell transformed by a recombinant DNA coding for a single-chain precursor of the double-chain insulin precursor and a leader peptide.

34. The double-chain insulin precursor according to claim 33 wherein the single-chain insulin precursor has the formula B-KR-Y-N-Pur-M-A, K is lysine and R is arginine.

35. The double-chain insulin precursor according to claim 32 wherein the insulin is selected from the group consisting of human insulin, porcine insulin and bovine insulin.

36. A double-chain insulin precursor having the formula A::B-N-X wherein A and B represent the A and B polypeptide chains, respectively, of insulin and :: represents two disulfide bonds established between the A and B chains, N is methionine or aspartic acid, and X is a chain of amino acid residues that comprises a purification sequence Pur and/or an additional polypeptide of interest, wherein Pur is a sequence of amino acid residues that can be recognized and bound by another molecule for in vitro separation of an insulin precursor containing the sequence from a mixture of molecules.

37. The double-chain insulin precursor according to claim 36 wherein the double-chain precursor is secreted by a yeast or fungus host cell transformed by a recombinant DNA coding for a single-chain precursor of the double-chain insulin precursor and a leader peptide.

38. The double-chain insulin precursor according to claim 37 wherein the single-chain precursor has the formula B-N-X-KR-A, K is lysine and R is arginine.

39. The double-chain insulin precursor according to claim 36 wherein the insulin is selected from the group consisting of human insulin, porcine insulin and bovine insulin.

40. A method for preparing insulin from a single-chain protein precursor having the general formula B-Z-A wherein B and A are the two polypeptide chains representing, respectively, the B- and A- chains of insulin, and Z is a polypeptide comprising at least one site for proteolytic cleavage in a transformed yeast or fungus host cell, the method comprising the steps of:
 transforming or transfecting a eukaryotic host cell with an expression vector expressing a DNA sequence encoding a single-chain protein precursor of insulin and comprising any one of SEQ ID NOs: 10 to 18, or a DNA sequence that encodes the same protein as encoded by any one of SEQ ID NOs: 10 to 18, and a leader peptide which directs the protein precursor into a secretion pathway of the host cell;
 cultivating the transformed host in a suitable culture medium;
 recovering from the culture medium a secreted double-chain insulin precursor having the formula -A::B or A::B- or -A::B-, resulting from proteolytic cleavage of the single-chain precursor by the host cell, wherein :: represents two disulfide bonds established between the A and B chains and "—" represents a retained portion of the Z polypeptide on the A and/or the B chain; and
 converting the secreted double-chain insulin precursor to insulin by treatment with a cleaving agent to remove the retained portions of the Z polypeptide.

41. A method according to claim 40 wherein the single-chain protein precursor is of the general formula (II): B-KR-X-M-A, wherein Z is KR-X-M, K is lysine, R is arginine, M is methionine, X represents a chain of amino acid residues sufficient in length to facilitate cleavage of the Z polypeptide in the host at the KR residues, and the secreted double-chain insulin precursor is X-M-A::B.

42. A method according to claim 41, wherein the converting step includes cleaving the secreted double-chain insulin precursor at the methionine residue with cyanogen bromide treatment to remove the X chain of amino acid residues.

43. A method according to claim 40 wherein the single-chain protein precursor is of the general formula (III): B-KR-Pur-M-A, wherein Z is KR-Pur-M, K is lysine, R is arginine, Pur is a purification sequence of amino acid residues that can be recognized and bound by another molecule for in vitro separation of the secreted double-chain insulin precursor from a mixture of molecules, M is methionine, and cleavage at the KR residues results in the secreted double-chain insulin precursor Pur-M-A::B.

44. A method according to claim 43, wherein the recovering step includes recovering the secreted double-chain insulin precursor by affinity-chromatography via the purification sequence Pur, and the converting step includes cleaving the recovered double-chain insulin precursor at the methionine residue with cyanogen bromide treatment.

45. A method according to claim 40 wherein the single-chain protein precursor is of the general formula (IV): B-KR-Y-M-A, wherein Z is KR-Y-M, K is lysine, R is arginine, Y is a second polypeptide of interest included in Z, and M is methionine, wherein cleavage at the KR residues results in the secreted double-chain insulin precursor Y-M-A::B.

46. A method according to claim 45, wherein the converting step includes releasing the second polypeptide Y from the secreted double-chain insulin precursor by cleaving at the methionine residue with cyanogen bromide treatment.

47. A method according to claim 40 wherein the single-chain protein precursor is of the general formula (V): B-KR-Y-N-Pur-M-A, wherein Z is KR-Y-N-Pur-M, K is lysine, R is arginine, Y is a second polypeptide of interest included in Z, N is methionine or aspartic acid, Pur is a purification sequence as defined in claim 43, M is methionine, and cleavage at the KR residues results in the secreted double-chain insulin precursor Y-N-Pur-M-A::B.

48. A method according to claim 47, wherein the recovering step includes recovering the secreted double-chain insulin precursor by affinity-chromatography via the purification sequence Pur, and the converting step includes cleaving the recovered double-chain insulin precursor at the methionine residue M with cyanogen bromide treatment, and releasing the second polypeptide Y by cleaving at the methionine residue N.

49. A method according to claim 40 wherein the single-chain protein precursor is of the general formula (VI): B-N-X-KR-A, wherein Z is N-X-KR, N is methionine or aspartic acid, K is lysine, R is arginine, X is as defined in claim 41, and cleavage at the KR residues results in the secreted double-chain insulin precursor A::B-N-X.

50. A method according to claim 49 wherein the X chain comprises at least either a purification sequence Pur or a second polypeptide Y, wherein Pur is a sequence of amino acid residues that can be recognized and bound by another molecule for in vitro separation of the secreted double-chain insulin precursor from a mixture of molecules.

51. A method according to claim 49 wherein the converting step includes cleaving the double-chain insulin precursor at the aspartic acid residue N by *Pseudomonas fragi* Me1 endopeptidase treatment to remove the X chain of amino acid residues.

52. A method according to claim 40 wherein the codons of the DNA sequence correspond to the most abundant transfer RNA's for each amino acid in the host.

53. A method according to claims 40 wherein the culture medium is malt-extract-cassamino acids culture medium.

* * * * *

SEQUENCE LISTING (1) GENERAL INFORMATION:

(iii) NUMBER OF SEQUENCES: 43

(2) INFORMATION FOR SEQ ID NO: 1:

(i) SEQUENCE CHARACTERISTICS:
       (A) LENGTH: 67 amino acids
       (B) TYPE: amino acid
       (C) STRANDEDNESS:
       (D) TOPOLOGY: unknown (xi) SEQUENCE DESCRIPTION: SEQ ID NO: 1:

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Lys Arg
            20                  25                  30

Glu Gln Lys Leu Ile Ser Glu Glu Asp Leu Val Asp Lys Arg Gly Ile
        35                  40                  45

Val Glu Gln Cys Cys Thr Ser Ile Cys Ser Leu Tyr Gln Leu Glu Asn
    50                  55                  60

Tyr Cys Asn
65

(2) INFORMATION FOR SEQ ID NO: 2:

(i) SEQUENCE CHARACTERISTICS:
       (A) LENGTH: 67 amino acids
       (B) TYPE: amino acid
       (C) STRANDEDNESS:
       (D) TOPOLOGY: unknown (xi) SEQUENCE DESCRIPTION: SEQ ID NO: 2:

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Lys Arg
            20                  25                  30

Glu Gln Lys Leu Ile Ser Glu Glu Asp Leu Val Asp Lys Met Gly Ile
        35                  40                  45

Val Glu Gln Cys Cys Thr Ser Ile Cys Ser Leu Tyr Gln Leu Glu Asn
    50                  55                  60

Tyr Cys Asn
65

(2) INFORMATION FOR SEQ ID NO: 3:

(i) SEQUENCE CHARACTERISTICS:
       (A) LENGTH: 83 amino acids
       (B) TYPE: amino acid
       (C) STRANDEDNESS:
       (D) TOPOLOGY: unknown (xi) SEQUENCE DESCRIPTION: SEQ ID NO: 3:

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Lys Arg
            20                  25                  30

Glu Gln Lys Leu Ile Ser Glu Glu Asp Leu Val Asp Met His Gly Leu
        35                  40                  45

-continued

```
Arg Ala Arg Asn Arg Ser Lys Thr Gly Pro Val Asp Lys Met Gly Ile
    50              55                  60

Val Glu Gln Cys Cys Thr Ser Ile Cys Ser Leu Tyr Gln Leu Glu Asn
65              70                  75                  80

Tyr Cys Asn
```

(2) INFORMATION FOR SEQ ID NO: 4:

(i) SEQUENCE CHARACTERISTICS:
        (A) LENGTH: 69 amino acids
        (B) TYPE: amino acid
        (C) STRANDEDNESS:
        (D) TOPOLOGY: unknown (xi) SEQUENCE DESCRIPTION: SEQ ID NO: 4:

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Lys Arg
            20                  25                  30

Gly Leu Arg Ala Arg Asn Arg Ser Lys Thr Gly Pro Val Asp Lys Met
        35                  40                  45

Gly Ile Val Glu Gln Cys Cys Thr Ser Ile Cys Ser Leu Tyr Gln Leu
    50                  55                  60

Glu Asn Tyr Cys Asn
65
```

(2) INFORMATION FOR SEQ ID NO: 5:

(i) SEQUENCE CHARACTERISTICS:
        (A) LENGTH: 67 amino acids
        (B) TYPE: amino acid
        (C) STRANDEDNESS:
        (D) TOPOLOGY: unknown (xi) SEQUENCE DESCRIPTION: SEQ ID NO: 5:

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Met His
            20                  25                  30

Glu Gln Lys Leu Ile Ser Glu Glu Asp Leu Val Asp Lys Arg Gly Ile
        35                  40                  45

Val Glu Gln Cys Cys Thr Ser Ile Cys Ser Leu Tyr Gln Leu Glu Asn
    50                  55                  60

Tyr Cys Asn
65
```

(2) INFORMATION FOR SEQ ID NO: 6:

(i) SEQUENCE CHARACTERISTICS:
        (A) LENGTH: 83 amino acids
        (B) TYPE: amino acid
        (C) STRANDEDNESS:
        (D) TOPOLOGY: unknown (xi) SEQUENCE DESCRIPTION: SEQ ID NO: 6:

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Met His
            20                  25                  30

Glu Gln Lys Leu Ile Ser Glu Glu Asp Leu Val Asp Met His Gly Leu
        35                  40                  45
```

```
Arg Ala Arg Asn Arg Ser Lys Thr Gly Pro Val Asp Lys Arg Gly Ile
         50                  55                  60

Val Glu Gln Cys Cys Thr Ser Ile Cys Ser Leu Tyr Gln Leu Glu Asn
 65                  70                  75                  80

Tyr Cys Asn
```

(2) INFORMATION FOR SEQ ID NO: 7:

(i) SEQUENCE CHARACTERISTICS:
        (A) LENGTH: 67 amino acids
        (B) TYPE: amino acid
        (C) STRANDEDNESS:
        (D) TOPOLOGY: unknown (xi) SEQUENCE DESCRIPTION: SEQ ID NO: 7:

```
Phe Val Asn Gln His Leu Cys Gly Ser His Leu Val Glu Ala Leu Tyr
 1                   5                  10                  15

Leu Val Cys Gly Glu Arg Gly Phe Phe Tyr Thr Pro Lys Ala Lys Arg
         20                  25                  30

Glu Gln Lys Leu Ile Ser Glu Glu Asp Leu Val Asp Lys Met Gly Ile
             35                  40                  45

Val Glu Gln Cys Cys Thr Ser Ile Cys Ser Leu Tyr Gln Leu Glu Asn
         50                  55                  60

Tyr Cys Asn
 65
```

(2) INFORMATION FOR SEQ ID NO: 8:

(i) SEQUENCE CHARACTERISTICS:
        (A) LENGTH: 83 amino acids
        (B) TYPE: amino acid
        (C) STRANDEDNESS:
        (D) TOPOLOGY: unknown (xi) SEQUENCE DESCRIPTION: SEQ ID NO: 8:

```
Phe Val Asn Gln His Leu Cys Gly Ser His Leu Val Glu Ala Leu Tyr
 1                   5                  10                  15

Leu Val Cys Gly Glu Arg Gly Phe Phe Tyr Thr Pro Lys Ala Lys Arg
         20                  25                  30

Glu Gln Lys Leu Ile Ser Glu Glu Asp Leu Val Asp Met His Gly Leu
             35                  40                  45

Arg Ala Arg Asn Arg Ser Lys Thr Gly Pro Val Asp Lys Met Gly Ile
         50                  55                  60

Val Glu Gln Cys Cys Thr Ser Ile Cys Ser Leu Tyr Gln Leu Glu Asn
 65                  70                  75                  80

Tyr Cys Asn
```

(2) INFORMATION FOR SEQ ID NO: 9:

(i) SEQUENCE CHARACTERISTICS:
        (A) LENGTH: 83 amino acids
        (B) TYPE: amino acid
        (C) STRANDEDNESS:
        (D) TOPOLOGY: unknown (xi) SEQUENCE DESCRIPTION: SEQ ID NO: 9:

```
Phe Val Asn Gln His Leu Cys Gly Ser His Leu Val Glu Ala Leu Tyr
 1                   5                  10                  15

Leu Val Cys Gly Glu Arg Gly Phe Phe Tyr Thr Pro Lys Ala Lys Arg
         20                  25                  30
```

Glu Gln Lys Leu Ile Ser Glu Glu Asp Leu Val Asp Met His Gly Leu
        35                  40                  45

Arg Ala Arg Asn Arg Ser Lys Thr Gly Pro Val Asp Lys Met Gly Ile
50                  55                  60

Val Glu Gln Cys Cys Ala Ser Val Cys Ser Leu Tyr Gln Leu Glu Asn
65                  70                  75                  80

Tyr Cys Asn (2) INFORMATION FOR SEQ ID NO: 10:

(i) SEQUENCE CHARACTERISTICS:
        (A) LENGTH: 204 base pairs
        (B) TYPE: nucleic acid
        (C) STRANDEDNESS: double
        (D) TOPOLOGY: linear (xi) SEQUENCE DESCRIPTION: SEQ ID NO: 10:

TTCGTTAACC AACACTTGTG TGGTTCTCAC TTGGTTGAAG CCTTGTACTT GGTTTGTGGT     60

GAAAGAGGTT TCTTCTACAC TCCAAAGACT ATGCATGAAC AAAAGTTGAT CTCTGAAGAA    120

GACTTGGTCG ACAAGAGAGG TATCGTTGAA CAATGTTGTA CTTCTATCTG TTCTTTGTAC    180

CAATTGGAAA ACTACTGTAA CTAA                                           204

(2) INFORMATION FOR SEQ ID NO: 11:

(i) SEQUENCE CHARACTERISTICS:
        (A) LENGTH: 204 base pairs
        (B) TYPE: nucleic acid
        (C) STRANDEDNESS: double
        (D) TOPOLOGY: linear (xi) SEQUENCE DESCRIPTION: SEQ ID NO: 11:

TTCGTTAACC AACACTTGTG TGGTTCTCAC TTGGTTGAAG CCTTGTACTT GGTTTGTGGT     60

GAAAGAGGTT TCTTCTACAC TCCAAAGACT AAGAGAGAAC AAAAGTTGAT CTCTGAAGAA    120

GACTTGGTCG ACAAGAGAGG TATCGTTGAA CAATGTTGTA CTTCTATCTG TTCTTTGTAC    180

CAATTGGAAA ACTACTGTAA CTAA                                           204

(2) INFORMATION FOR SEQ ID NO: 12:

(i) SEQUENCE CHARACTERISTICS:
        (A) LENGTH: 204 base pairs
        (B) TYPE: nucleic acid
        (C) STRANDEDNESS: double
        (D) TOPOLOGY: linear (xi) SEQUENCE DESCRIPTION: SEQ ID NO: 12:

TTCGTTAACC AACACTTGTG TGGTTCTCAC TTGGTTGAAG CCTTGTACTT GGTTTGTGGT     60

GAAAGAGGTT TCTTCTACAC TCCAAAGACT AAGAGAGAAC AAAAGTTGAT CTCTGAAGAA    120

GACTTGGTCG ACAAGATGGG TATCGTTGAA CAATGTTGTA CTTCTATCTG TTCTTTGTAC    180

CAATTGGAAA ACTACTGTAA CTAA                                           204

(2) INFORMATION FOR SEQ ID NO: 13:

(i) SEQUENCE CHARACTERISTICS:
        (A) LENGTH: 252 base pairs
        (B) TYPE: nucleic acid
        (C) STRANDEDNESS: double
        (D) TOPOLOGY: linear (xi) SEQUENCE DESCRIPTION: SEQ ID NO: 13:

```
TTCGTTAACC AACACTTGTG TGGTTCTCAC TTGGTTGAAG CCTTGTACTT GGTTTGTGGT      60

GAAAGAGGTT TCTTCTACAC TCCAAAGACT ATGCATGAAC AAAAGTTGAT CTCTGAAGAA     120

GACTTGGTCG ACATGCATGG TTTGAGAGCT AGAAACAGAT CTAAGACCGG TCCAGTCGAC     180

AAGAGAGGTA TCGTTGAACA ATGTTGTACT TCTATCTGTT CTTTGTACCA ATTGGAAAAC     240

TACTGTAACT AA                                                        252
```

(2) INFORMATION FOR SEQ ID NO: 14:

(i) SEQUENCE CHARACTERISTICS:
        (A) LENGTH: 252 base pairs
        (B) TYPE: nucleic acid
        (C) STRANDEDNESS: double
        (D) TOPOLOGY: linear (xi) SEQUENCE DESCRIPTION: SEQ ID NO: 14:

```
TTCGTTAACC AACACTTGTG TGGTTCTCAC TTGGTTGAAG CCTTGTACTT GGTTTGTGGT      60

GAAAGAGGTT TCTTCTACAC TCCAAAGACT AAGAGAGAAC AAAAGTTGAT CTCTGAAGAA     120

GACTTGGTCG ACATGCATGG TTTGAGAGCT AGAAACAGAT CTAAGACCGG TCCAGTCGAC     180

AAGATGGGTA TCGTTGAACA ATGTTGTACT TCTATCTGTT CTTTGTACCA ATTGGAAAAC     240

TACTGTAACT AA                                                        252
```

(2) INFORMATION FOR SEQ ID NO: 15:

(i) SEQUENCE CHARACTERISTICS:
        (A) LENGTH: 210 base pairs
        (B) TYPE: nucleic acid
        (C) STRANDEDNESS: double
        (D) TOPOLOGY: linear (xi) SEQUENCE DESCRIPTION: SEQ ID NO: 15:

```
TTCGTTAACC AACACTTGTG TGGTTCTCAC TTGGTTGAAG CCTTGTACTT GGTTTGTGGT      60

GAAAGAGGTT TCTTCTACAC TCCAAAGACT AAGAGAGGTT TGAGAGCTAG AAACAGATCT     120

AAGACCGGTC CAGTCGACAA GATGGGTATC GTTGAACAAT GTTGTACTTC TATCTGTTCT     180

TTGTACCAAT TGGAAAACTA CTGTAACTAA                                     210
```

(2) INFORMATION FOR SEQ ID NO: 16:

(i) SEQUENCE CHARACTERISTICS:
        (A) LENGTH: 204 base pairs
        (B) TYPE: nucleic acid
        (C) STRANDEDNESS: double
        (D) TOPOLOGY: linear (xi) SEQUENCE DESCRIPTION: SEQ ID NO: 16:

```
TTCGTTAACC AACACTTGTG TGGTTCTCAC TTGGTTGAAG CCTTGTACTT GGTTTGTGGT      60

GAAAGAGGTT TCTTCTACAC TCCAAAGGCC AAGAGAGAAC AAAAGTTGAT CTCTGAAGAA     120

GACTTGGTCG ACAAGATGGG TATCGTTGAA CAATGTTGTA CTTCTATCTG TTCTTTGTAC     180

CAATTGGAAA ACTACTGTAA CTAA                                           204
```

(2) INFORMATION FOR SEQ ID NO: 17:

(i) SEQUENCE CHARACTERISTICS:
        (A) LENGTH: 252 base pairs
        (B) TYPE: nucleic acid
        (C) STRANDEDNESS: double
        (D) TOPOLOGY: linear (xi) SEQUENCE DESCRIPTION: SEQ ID NO: 17:

```
TTCGTTAACC AACACTTGTG TGGTTCTCAC TTGGTTGAAG CCTTGTACTT GGTTTGTGGT      60
GAAAGAGGTT TCTTCTACAC TCCAAAGGCC AAGAGAGAAC AAAAGTTGAT CTCTGAAGAA     120
GACTTGGTCG ACATGCATGG TTTGAGAGCT AGAAACAGAT CTAAGACCGG TCCAGTCGAC     180
AAGATGGGTA TCGTTGAACA ATGTTGTACT TCTATCTGTT CTTTGTACCA ATTGGAAAAC     240
TACTGTAACT AA                                                        252
```

(2) INFORMATION FOR SEQ ID NO: 18:

(i) SEQUENCE CHARACTERISTICS:
        (A) LENGTH: 252 base pairs
        (B) TYPE: nucleic acid
        (C) STRANDEDNESS: double
        (D) TOPOLOGY: linear (xi) SEQUENCE DESCRIPTION: SEQ ID NO: 18:

```
TTCGTTAACC AACACTTGTG TGGTTCTCAC TTGGTTGAAG CCTTGTACTT GGTTTGTGGT      60
GAAAGAGGTT TCTTCTACAC TCCAAAGGCC AAGAGAGAAC AAAAGTTGAT CTCTGAAGAA     120
GACTTGGTCG ACATGCATGG TTTGAGAGCT AGAAACAGAT CTAAGACCGG TCCAGTCGAC     180
AAGATGGGTA TCGTTGAACA ATGTTGTGCT TCTGTTTGTT CTTTGTACCA ATTGGAAAAC     240
TACTGTAACT AA                                                        252
```

(2) INFORMATION FOR SEQ ID NO: 19:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (xi) SEQUENCE DESCRIPTION: SEQ ID NO: 19:

```
CTACACTCCA AAGACTAAGA GAGGTATCGT TGAACAATGT TGTACTTCTA TCTGTTCTTT      60
GTACCAATTG GAAAACTACT GTAACTAATA AG                                   92
```

(2) INFORMATION FOR SEQ ID NO: 20:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (xi) SEQUENCE DESCRIPTION: SEQ ID NO: 20:

```
GATCCTTATT AGTTACAGTA GTTTTCCAAT TGGTACAAAG AACAGATAGA AGTACAACAT      60
TCTTCAACGA TACCTCTCTT                                                 80
```

(2) INFORMATION FOR SEQ ID NO: 21:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (xi) SEQUENCE DESCRIPTION: SEQ ID NO: 21:

```
AGCTTTCGTT AACCAACACT TGTGTGGTTC TCACTTGGTT GAAGCCTTGT ACTTGGTTTG      60
TGGTGAAAGA GGTTTCTT                                                   78
```

(2) INFORMATION FOR SEQ ID NO: 22:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (xi) SEQUENCE DESCRIPTION: SEQ ID NO: 22:

```
ACTCTTTGGA GTGTAGAAGA AACCTCTTTC ACCACAAACC AAGTACAAGG CTTCAACCAA        60

GTGAGAACCA CACAAGTCTT GGTTAACGAA                                        90
```

(2) INFORMATION FOR SEQ ID NO: 23:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (xi) SEQUENCE DESCRIPTION: SEQ ID NO: 23:

```
CTACACTCCA AAGACTATGC ATGAACAAAA GTTGATCTCT GAAGAAGACT TGGTCGACAA        60

GAGAGGTATG CTTGAACAAT GTTGTACTTC TATCTGTTCT TTGTACCAAT GGAAAACTA       120

CTGTAACTAA TAAG                                                        134
```

(2) INFORMATION FOR SEQ ID NO: 24:

(i) SEQUENCE CHARACTERISTICS:
        (A) LENGTH: 122 base pairs
        (B) TYPE: nucleic acid
        (C) STRANDEDNESS: single
        (D) TOPOLOGY: linear (xi) SEQUENCE DESCRIPTION: SEQ ID NO: 24:

```
GATCCTTATT AGTTACAGTA GTTTTCCAAT TGGTACAAAG AACAGATAGA AGTACAACAT        60

TGTTCAACGA TACCTCTCTT GTCGACCAAG TCTTCTTCAG AGATCAACTT TTGTTCATGC       120

AT                                                                     122
```

(2) INFORMATION FOR SEQ ID NO: 25:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 25:

```
AAATACTACT ATTGCCAGC                                                    19
```

(2) INFORMATION FOR SEQ ID NO: 26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 26:

```
CATACACAAT ATAAACGACC                                                   20
```

(2) INFORMATION FOR SEQ ID NO: 27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 27:

CAAGGTAGAC AAGCCGAC                                              18

(2) INFORMATION FOR SEQ ID NO: 28:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 28:

ACTAAGAGAG AACAAAAGTT GATCTCTG                            28

(2) INFORMATION FOR SEQ ID NO: 29:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 29:

TTCTCTCTTA GTCTTTGGAG TGTAGAAG                            28

(2) INFORMATION FOR SEQ ID NO: 30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 30:

GACAAGATGG GTATCGTTGA ACAA                                  24

(2) INFORMATION FOR SEQ ID NO: 31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 31:

ACCCATCTTG TCGACCAAGT CTTC                                  24

(2) INFORMATION FOR SEQ ID NO: 32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 32:

AAGAGAGGTT TGAGAGCTAG AAAC                                  24

(2) INFORMATION FOR SEQ ID NO: 33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 33:

CAAACCTCTC TTAGTCTTTG GAGT                                  24

(2) INFORMATION FOR SEQ ID NO: 34:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 34:

AAGGCCAAGA GAGAACAAAA GTTGATC                            27

(2) INFORMATION FOR SEQ ID NO: 35:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 35:

CTTGGCCTTT GGAGTGTAGA AGAAACCT                         28

(2) INFORMATION FOR SEQ ID NO: 36:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 36:

GTTGTGCTTC TGTTTGTTCT TTGTACCAA                      29

(2) INFORMATION FOR SEQ ID NO: 37:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 37:

GAACAAACAG AAGCACAACA TTGTTCAACG                   30

(2) INFORMATION FOR SEQ ID NO: 38:

(i) SEQUENCE CHARACTERISTICS:
        (A) LENGTH: 4 amino acids
        (B) TYPE: amino acid
        (C) STRANDEDNESS:
        (D) TOPOLOGY: unknown (xi) SEQUENCE DESCRIPTION: SEQ ID NO: 38:

Glu Ala Glu Ala
1

```
(2) INFORMATION FOR SEQ ID NO: 39:

(i) SEQUENCE CHARACTERISTICS:
        (A) LENGTH: 13 base pairs
        (B) TYPE: nucleic acid
        (C) STRANDEDNESS: double
        (D) TOPOLOGY: linear (xi) SEQUENCE DESCRIPTION: SEQ ID NO: 39:

GAGGCTGAAG CTT                                                            13

(2) INFORMATION FOR SEQ ID NO: 40:

(i) SEQUENCE CHARACTERISTICS:
        (A) LENGTH: 7 amino acids
        (B) TYPE: amino acid
        (C) STRANDEDNESS:
        (D) TOPOLOGY: unknown (xi) SEQUENCE DESCRIPTION: SEQ ID NO: 40:

Lys Arg Glu Ala Glu Ala Phe
1               5

(2) INFORMATION FOR SEQ ID NO: 41:

(i) SEQUENCE CHARACTERISTICS:
        (A) LENGTH: 21 base pairs
        (B) TYPE: nucleic acid
        (C) STRANDEDNESS: double
        (D) TOPOLOGY: circular (xi) SEQUENCE DESCRIPTION: SEQ ID NO: 41:

AAGAGAGAGG CTGAAGCTTT C                                                   21

(2) INFORMATION FOR SEQ ID NO: 42:

(i) SEQUENCE CHARACTERISTICS:
        (A) LENGTH: 53 amino acids
        (B) TYPE: amino acid
        (C) STRANDEDNESS:
        (D) TOPOLOGY: unknown (xi) SEQUENCE DESCRIPTION: SEQ ID NO: 42:

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Lys Arg
                20                  25                  30

Gly Ile Val Glu Gln Cys Cys Thr Ser Ile Cys Ser Leu Tyr Gln Leu
            35                  40                  45

Glu Asn Tyr Cys Asn
    50

(2) INFORMATION FOR SEQ ID NO: 43:

(i) SEQUENCE CHARACTERISTICS:
        (A) LENGTH: 162 base pairs
        (B) TYPE: nucleic acid
        (C) STRANDEDNESS: double
        (D) TOPOLOGY: linear (xi) SEQUENCE DESCRIPTION: SEQ ID NO: 43:

TTCGTTAACC AACACTTGTG TGGTTCTCAC TTGGTTGAAG CCTTGTACTT GGTTTGTGGT          60

GAAAGAGGTT TCTTCTACAC TCCAAAGACT AAGAGAGGTA TCGTTGAACA ATGTTGTACT         120

TCTATCTGTT CTTTGTACCA ATTGGAAAAC TACTGTAACT AA                           162
```